United States Patent
Ali et al.

(10) Patent No.: US 10,314,859 B2
(45) Date of Patent: *Jun. 11, 2019

(54) USE OF GASTROINTESTINALLY ADMINISTERED POROUS ENTERON SORBENT POLYMERS TO PREVENT OR TREAT RADIATION INDUCED MUCOSITIS, ESOPHAGITIS, ENTERITIS, COLITIS, AND GASTROINTESTINAL ACUTE RADIATION SYNDROME

(71) Applicant: Cytosorbents Corporation, Monmouth Junction, NJ (US)

(72) Inventors: Humayra Begum Ali, Princeton Junction, NJ (US); Thomas D. Golobish, Princeton, NJ (US); Vincent J. Capponi, Monmouth Junction, NJ (US); Phillip P. Chan, Cherry Hill, NJ (US); Wei Tai Young, Hillsborough, NJ (US); Andrew Robert Scheirer, Bethlehem, PA (US)

(73) Assignee: Cytosorbents Corporation, Monmouth Junction, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/886,978

(22) Filed: Feb. 2, 2018

(65) Prior Publication Data

US 2018/0169138 A1    Jun. 21, 2018

Related U.S. Application Data

(63) Continuation of application No. 15/515,328, filed as application No. PCT/US2015/053622 on Oct. 2, 2015, now Pat. No. 9,931,357.

(60) Provisional application No. 62/058,864, filed on Oct. 2, 2014.

(51) Int. Cl.

| | |
|---|---|
| *A61M 31/00* | (2006.01) |
| *A61K 31/74* | (2006.01) |
| *A61K 31/765* | (2006.01) |
| *A61P 1/06* | (2006.01) |
| *A61P 1/04* | (2006.01) |
| *A61P 1/00* | (2006.01) |
| *A61K 9/00* | (2006.01) |
| *A61K 31/79* | (2006.01) |
| *A61K 31/75* | (2006.01) |

(52) U.S. Cl.
CPC ......... *A61K 31/765* (2013.01); *A61K 9/0053* (2013.01); *A61K 31/75* (2013.01); *A61K 31/79* (2013.01); *A61P 1/00* (2018.01); *A61P 1/04* (2018.01); *A61P 1/06* (2018.01)

(58) Field of Classification Search
None
See application file for complete search history.

(56) References Cited

U.S. PATENT DOCUMENTS

| | | | |
|---|---|---|---|
| 7,553,325 | B2 | 6/2009 | Stinson |
| 2011/0009344 | A1 | 1/2011 | Benner et al. |
| 2011/0212172 | A1* | 9/2011 | Kellum ............... A61K 31/75 424/464 |
| 2013/0011824 | A1* | 1/2013 | Chan .................. A01N 1/0263 435/2 |
| 2013/0195792 | A1* | 8/2013 | Chan ................... A61K 31/74 424/78.31 |
| 2014/0017309 | A1 | 1/2014 | Kellum et al. |

FOREIGN PATENT DOCUMENTS

| | | |
|---|---|---|
| CN | 101307149 A | 11/2008 |
| CN | 103037869 A | 4/2013 |
| JP | 2003502465 A | 1/2003 |
| WO | WO 02/056895 | 7/2002 |
| WO | 2010111294 A1 | 9/2010 |
| WO | 2011123767 A1 | 10/2011 |
| WO | WO 2014/005039 | 1/2014 |

OTHER PUBLICATIONS

Valuckaite et al.,"Oral PEG 15-20 Protects the Intestine Against Radiation: Role of Lipid Rafts", Am. J. Physiol. Gastrointest. Liver Physiol. 297, 2009, pp. G1041-G1052 [Cited in Parent].
Dubois et al., "Prospects for management of gastrointestinal injury associated with the acute radiation syndrome" Gastroenterology, 95, Aug. 1988, pp. 500-507 [Cited in Parent].
Hauer-Jensen, "Late Radiation Injury of the Small Intestine Clinical, Pathophysiologic and Radiobiologic Aspects: A review", Acta Oncologica,1990 29:4, pp. 401-415 DOI: 10.3109/02841869009090022 [Cited in Parent].
Johnson et al., "Pelvic Radiation Disease", Clinical Radiology, 45,1992, pp. 4-12 [Cited in Parent].
Kao, "Intestinal Complications of Radiotherapy in Gynecologic Malignancy—Clinical Presentation and Management", International Journal of Gynecology & Obstetrics, 49 (Suppl),1995, pp. S69-S75 [Cited in Parent].
Hauer-Jensen et al., "Bowel injury: Current and Evolving Management Strategies", Seminars in Radiation Oncology, vol. 13, No. 3, Jul. 2003, pp. 357-371 [Cited in Parent].
Andreyev, "Gastrointestinal Complications of Pelvic Radiotherapy: Are They of Any Importance?" 54,Gut 2005, pp. 1051-1054 [Cited in Parent].
Brizel, et al.,"Phase III Randomized Trial of Amifostine as a Radioprotector in Head and Neck Cancer", Journal of Clinical Oncology, vol. 18, No. 19, Oct. 2000, pp. 3339-3345 [Cited in Parent].

(Continued)

*Primary Examiner* — Jeffrey T. Palenik
(74) *Attorney, Agent, or Firm* — BakerHostetler

(57) ABSTRACT

Disclosed herein are compositions and methods for preventing or treating acute or chronic oral mucositis, esophagitis, enteritis, colitis, or gastrointestinal acute radiation syndrome (GI-ARS) caused by radiation exposure, using one or more enteron sorbent polymers administered gastrointestinally (e.g. orally, via feeding or gastric tube, via ostomy, or rectally).

22 Claims, 10 Drawing Sheets

(56) References Cited

OTHER PUBLICATIONS

Cohen, et al., "Prevention and Treatment of Radiation Injuries—The role of the Renin-Angiotensin System" Heigelberg: Springer-Verlag, 2008, pp. 69-76 [Cited in Parent].

Pennison et al., "Targeting Transforming Growth Factor-Beta Signaling" Current Opinion in Oncology,19, 2007, pp. 579-585 [Cited in Parent].

* cited by examiner

Figure 1: Pore Volume vs. Pore Diameter Plot (dV/dD vs. D) for Adsorbent CY12030 Measured by Nitrogen Desorption Isotherm Figure 2: Pore Volume vs. Pore Diameter Plot (dV/dlogD vs. D) for Adsorbent CY12030 Measured by Nitrogen Desorption Isotherm Figure 3: Pore Volume vs. Pore Diameter Plot (dV/dD vs. D) for Adsorbent CY12031 Measured by Mercury Intrusion Figure 4: Pore Volume vs. Pore Diameter Plot
(dV/dD vs. D) for Adsorbent CY12031 Measured by Mercury Intrusion

USE OF GASTROINTESTINALLY ADMINISTERED POROUS ENTERON SORBENT POLYMERS TO PREVENT OR TREAT RADIATION INDUCED MUCOSITIS, ESOPHAGITIS, ENTERITIS, COLITIS, AND GASTROINTESTINAL ACUTE RADIATION SYNDROME

CROSS REFERENCE TO RELATED APPLICATIONS

This application is a continuation application of U.S. patent application Ser. No. 15/515,328, filed Mar. 29, 2017, now published U.S. Patent Application No. 2017-0216345, which is a National Stage Application filed under 35 U.S.C. § 371 of International Application No. PCT/US2015/053622, filed Oct. 2, 2015, which claims the benefit of U.S. Provisional Application No. 62/058,864, filed Oct. 2, 2014; the disclosures of which are incorporated herein by reference in their entireties.

TECHNICAL FIELD

The disclosed inventions are in the field of porous enteron sorbent polymers. The disclosed inventions are also in the field of reducing, preventing, and/or treating oral mucositis, esophagitis, radiation enteritis, colitis and gastrointestinal acute radiation syndrome.

BACKGROUND

Wide presence of radioactive material for therapeutic, energy, or weapons underscores the need for medical preparedness for effective treatment of either accidental or intentional exposure. High energy radiation exposure (e.g. gamma radiation or X-rays) from cancer radiotherapy, or from acute radiation exposure, such as from the broad dissemination of radioactive materials in water or air (e.g. a "dirty bomb", a nuclear power catastrophe, or a nuclear explosion) can penetrate the body and cause harmful effects such as cell death and tissue damage. Cosmic rays and solar flares are another form of high energy radiation experienced during solar flares, at high altitudes and in outer space, which can lead to similar tissue injury. When the gastrointestinal (GI) tract is affected, radiation can lead to oral mucositis (head and neck radiation), esophagitis typically thoracic radiation), and radiation enteritis and colitis (due to abdominal and pelvic radiation), and more broadly, gastrointestinal acute radiation syndrome (GI-ARS). Currently there is no medical therapy or countermeasure approved to prevent, treat or mitigate radiation toxicity post-exposure, other than secondary and supportive care.

One of the acute physiological effects of irradiation is acute radiation syndrome (ARS), which first manifests in the gastrointestinal tract (GI-ARS). The acute phase occurs within days of radiation exposure, resulting from loss of intestinal clonogenic cells that lead to loss of epithelial crypts and ulceration. Symptoms and complications include weight loss, diarrhea, dehydration, susceptibility to infection, and translocation of bacteria and toxins as the intestinal mucosal barrier is compromised. Bacterial translocation from the intestine to blood and endotoxemia can lead to septic shock and death.

Radiation injury can also lead to delayed effects of acute radiation exposure (GI-DEARE). Similar to ARS, delayed effects of radiation exposure also have adverse health effects. This is evident from the Japanese survivors of high-dose radiation exposure, and also from radiation onco-therapy. Patients receiving radiation cancer treatment can frequently develop both acute and delayed GI enteropathies months and years post-therapy. In the delayed effects, there is a high incidence of GI symptoms of diarrhea, constipation, obstruction, fistulation, severe inflammatory response syndrome and sepsis, occurring in 50% of the patients with pelvic tumors receiving therapy.

Characterization of GI-ARS links to other syndromes, such as the hematopoetic system (H-ARS). All radiation doses that induce GI-ARS will have a major impact on bone marrow. This will affect the severity of GI inflammation and infection due to bacterial translocation through the impaired gut epithelium. The major organ sequelae to high-dose radiation involve other organ damage as well. Lung injury, for example, results from the DEARE. Cytokines, bacterial toxins and other inflammatory mediators play an important role in the illness. Decreasing inflammation may offer a promising therapy. For example, a number of studies correlated reduction of inflammation with anti-cancer efficacy.

Each of these conditions is typically associated with high morbidity and mortality. Therefore, it is imperative to come up with treatments for the prevention (termed a radioprotector) and mitigation (termed a mitigator) of both the acute and delayed adverse effects of radiation exposure.

SUMMARY

Enteron sorbent polymers are uniquely suited to prevent or treat these conditions. Enteron sorbent polymer are novel gastrointestinally-administered (e.g. administration via oral, nasogastric or gastric tube, ostomy, or rectal routes), topical anti-inflammatory therapies for the GI tract that uses non-absorbable, highly-porous enteron sorbent polymers. Enteron sorbent polymers sequester intra-luminal cytokines, bacterial toxins and other mediators based on pore capture and surface adsorption and excrete them from the body. Enteron sorbent polymers can potentially reduce the risk of death in GI-ARS by reducing intestinal inflammation, gut permeability, bacterial and toxin translocation from the gut lumen to the systemic circulation, symptoms of enterocolitis such as diarrhea, the systemic inflammatory response syndrome, and septicemia.

In radiation cancer treatment, enteron sorbent polymers are gamma stable and radio-lucent and should remain stable and not interfere with radiotherapy. By mitigating GI enteritis and other associated conditions, enteron sorbent polymers may be able to minimize adverse event related radiation treatment de-escalation. Alternatively, it can aide in escalation of the radiation dose and concurrent chemotherapy aimed at improving tumor killing. Enteron sorbent polymers can serve as a radioprotector and/or a radiation mitigator post-exposure.

In prophylaxis of radiation enteritis due to mass radiation exposure or during a space mission, enteron sorbent polymers can be self-administered. They can also serve as a GI radiation mitigator after a high-dose exposure.

Preferred enteron sorbent polymers include cross-linked polymeric materials derived from the reaction of a cross-linker with one or more of the following polymerizable monomers: divinyl-benzene, styrene, ethylstyrene, acrylonitrile, butyl methacrylate, octyl methacrylate, butyl acrylate, octyl acrylate, cetyl methacrylate, cetyl acrylate, ethyl methacrylate, ethyl acrylate, vinyltoluene, vinylnaphthalene, vinylbenzyl alcohol, vinylformamide, methyl methacrylate, and methyl acrylate.

In certain embodiments, the solid form of the enteron sorbent polymer is characteristically porous. Some solid forms are characterized as having a pore structure having a total volume of pore sizes in the range of from 10 Å to 250,000 Å greater than 0.3 cc/g and less than 3.0 cc/g dry polymer; wherein the ratio of pore volume between 10 Å to 250,000 Å in diameter to pore volume between 250 Å to 250,000 Å in diameter of the cross-linked polymeric material is smaller than 7:1 and wherein the ratio of pore volume between 10 Å to 250,000 Å in diameter to pore volume between 50 Å to 250,000 Å in diameter of the cross-linked polymeric material is less than 2:1.

In certain embodiments, the enteron sorbent polymers can be made in bead form having a diameter in the range of 0.1 microns to 2 centimeters. Certain polymers are in the form of powder, beads or other regular or irregularly shaped particulates.

In some methods, the undesirable molecules are inflammatory mediators and stimulators comprise cytokines, superantigens, monokines, chemokines, interferons, free radicals, proteases, arachidonic acid metabolites, prostacyclins, beta endorphins, anandimide, 2-arachadonylglycerol, tetrahydrobiopterin, serotonin, histamine, bradykinin, soluble CD40 ligand, bioactive lipids, oxidized lipids, cell-free hemoglobin, growth factors, glycoproteins, prions, toxins, bacterial and viral toxins, endotoxins, drugs, vasoactive substances, foreign antigens, and antibodies.

Some methods of the invention can be performed such that the enteron sorbent polymer is gastrointestinally administered (e.g. orally, rectally, via nasogastric or gastric tube, or via ostomy within the human body).

In some embodiments, the plurality of solid forms of enteron sorbent polymer comprises particles having a diameter in the range for 0.1 micrometers to 2 centimeters.

Preferred enteron sorbent polymers are biocompatible.

In still yet another further embodiment, the present invention relates to a method of manufacturing enteron sorbent polymer comprising a biocompatible surface coated polymer system comprising an organic phase and an aqueous phase, the method comprising: forming the organic phase comprising polymerizable monomers and at least one initiator; forming the aqueous phase comprising at least one dispersant agent, at least one free radical inhibitor, and at least one buffering agent; dispersing the organic phase into the aqueous phase by agitation to form a suspension of organic droplets; and polymerizing the organic phase by heating the suspension of the organic phase droplets coated with the dispersing agent to thereby form the biocompatible surface coating on the enteron sorbent polymer.

In another embodiment, the present invention relates to an enteron sorbent polymer with a biocompatible coating comprising at least one crosslinking agent for making the enteron sorbent polymer and at least one dispersing agent whereby the dispersing agent forms a biocompatible surface on the enteron sorbent polymer.

In another embodiment, the biocompatibilizing polymer comprises poly(N-vinylpyrrolidinone). In still another embodiment, the biocompatibilizing polymer is selected from a group comprising poly(hydroxyethyl methacrylate), poly(hydroxyethyl acrylate), poly(dimethylaminoethyl methacrylate), salts of poly(acrylic acid), salts of poly (methacrylic acid), poly(diethylaminoethyl methacrylate), poly(hydroxypropyl methacrylate), poly(hydroxypropyl acrylate), poly(N-vinylpyrrolidinone), poly(vinyl alcohol) and mixtures thereof. In another embodiment, the salts may be sodium and potassium salts and in still another embodiment, the salts are water-soluble salts.

In yet another embodiment, the dispersing agent is selected from a group comprising hydroxyethyl cellulose, hydroxypopyl cellulose, poly(hydroxyethyl methacrylate), poly(hydroxyethyl acrylate), poly(hydroxypropyl methacrylate), poly(hydroxypropyl acrylate), poly(dimethylaminoethyl methacrylate), poly(dimethylaminoethyl acrylate), poly(diethylamimoethyl methacrylate), poly(diethylaminoethyl acrylate), poly(vinyl alcohol), salts of poly(methacrylic acid), and salts of poly(acrylic acid) and mixtures thereof.

Certain enteron sorbent polymers useful in the invention are porous polymers prepared from the polymerizable and copolymerizable monomers of styrene, divinylbenzene, ethylvinylbenzene, and the acrylate and methacrylate monomers such as those listed below by manufacturer. Rohm and Haas Company, (now part of Dow Chemical Company): (i) porous enteron sorbent polymers such as Amberlite™ XAD-1, Amberlite™ XAD-2, Amberlite™ XAD-4, Amberlite™ XAD-7, Amberlite™ XAD-7HP, Amberlite™ XAD-8, Amberlite™ XAD-16, Amberlite™ XAD-16 HP, Amberlite™ XAD-18, Amberlite™ XAD-200, Amberlite™ XAD-1180, Amberlite™ XAD-2000, Amberlite™ XAD-2005, Amberlite™ XAD-2010, Amberlite™ XAD-761, and Amberlite™ XE-305, and chromatographic grade enteron sorbent polymers such as Amberchrom™ CG 71,s,m,c, Amberchrom™ CG 161,s,m,c, Amberchrom™ CG 300,s,m,c, and Amberchrom™ CG 1000,s,m,c. Dow Chemical Company: Dowex™ Optipore™ L-493, Dowex™ Optipore™ V-493, Dowex™ Optipore™ V-502, Dowex™ Optipore™ L-285, Dowex™ Optipore™ L-323, and Dowex™ Optipore™ V-503. Lanxess (formerly Bayer and Sybron): Lewatit™ VPOC 1064 MD PH, Lewatit™ VPOC 1163, Lewatit™ OC EP 63, Lewatit™ S 6328A, Lewatit™ OC 1066, and Lewatit™ 60/150 MIBK. Mitsubishi Chemical Corporation: Diaion™ HP 10, Diaion™ HP 20, Diaion™ HP 21, Diaion™ HP 30, Diaion™ HP 40, Diaion™ HP 50, Diaion™ SP70, Diaion™ SP 205, Diaion™ SP 206, Diaion™ SP 207, Diaion™ SP 700, Diaion™ SP 800, Diaion™ SP 825, Diaion™ SP 850, Diaion™ SP 875, Diaion™ HP 1MG, Diaion™ HP 2MG, Diaion™ CHP 55A, Diaion™ CHP 55Y, Diaion™ CHP 20A, Diaion™ CHP 20Y, Diaion™ CHP 2MGY, Diaion™ CHP 20P, Diaion™ HP 20SS, Diaion™ SP 20SS, Diaion™ SP 207SS. Purolite Company: Purosorb™ AP 250 and Purosorb™ AP 400, and Kaneka Corp. Lixelle beads.

The general description and the following detailed description are exemplary and explanatory only and are not restrictive of the invention, as defined in the appended claims. Other aspects of the present invention will be apparent to those skilled in the art in view of the detailed description of the invention as provided herein.

BRIEF DESCRIPTION OF THE DRAWINGS

The summary, as well as the following detailed description, is further understood when read in conjunction with the appended drawings. For the purpose of illustrating the invention, there are shown in the drawings exemplary embodiments of the invention; however, the invention is not limited to the specific methods, compositions, and devices disclosed. In addition, the drawings are not necessarily drawn to scale. In the drawings.

DETAILED DESCRIPTION OF ILLUSTRATIVE EMBODIMENTS

Figure 1:
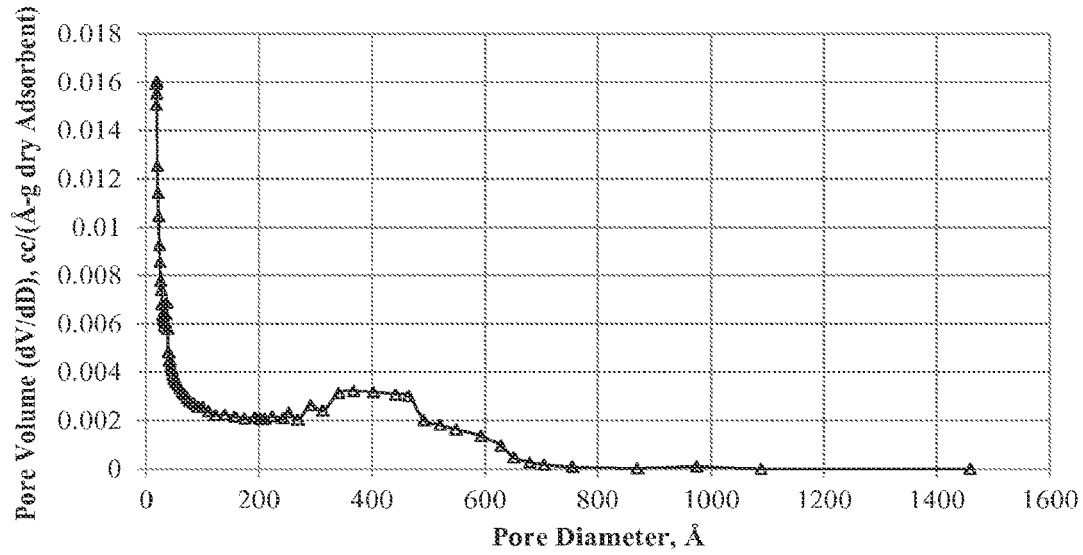
FIG. 1 illustrates a Pore Volume vs. Pore Diameter Plot, (dV/dD vs. D) for Adsorbent CY12030 Measured by Nitrogen Desorption Isotherm.
Figure 2:
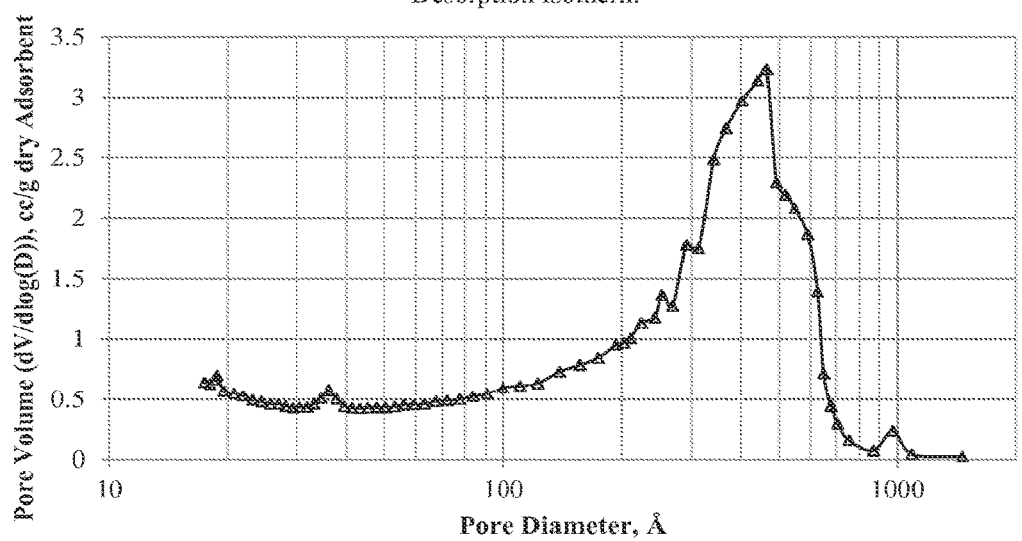
FIG. 2 illustrates a Pore Volume vs. Pore Diameter Plot, (dV/d log D vs. D) for Adsorbent CY12030 Measured by Nitrogen Desorption Isotherm.
Figure 3:
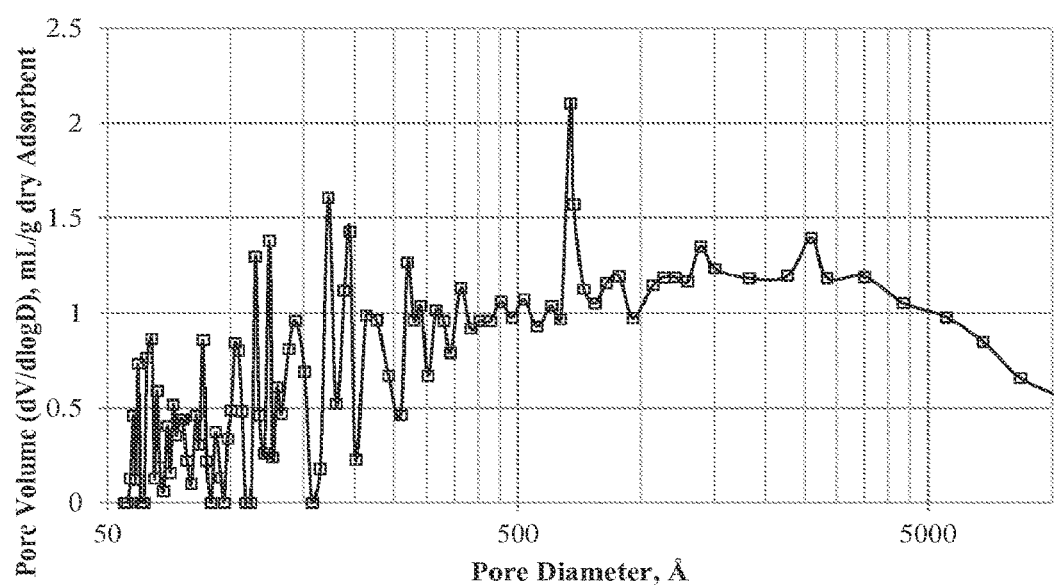
FIG. 3 illustrates a Pore Volume vs. Pore Diameter Plot, (dV/dD vs. D) for Adsorbent CY12031 Measured by Mercury Intrusion.
Figure 4:
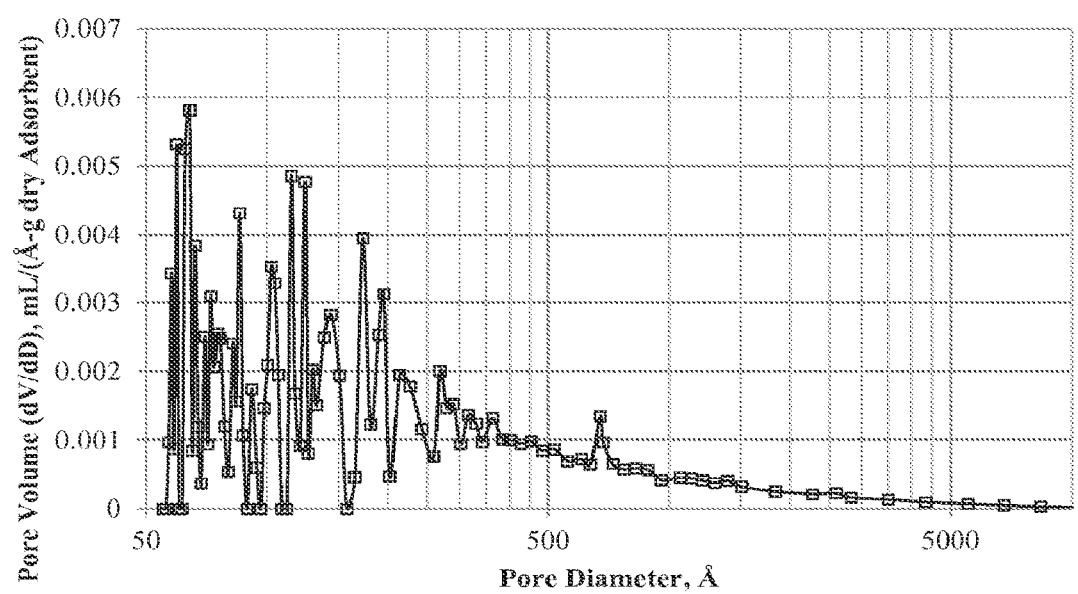
FIG. 4 illustrates a Pore Volume vs. Pore Diameter Plot, (dV/dD vs. D) for Adsorbent CY12031 Measured by Mercury Intrusion.

The present invention may be understood more readily by reference to the following detailed description taken in connection with the accompanying figures and examples, which form a part of this disclosure. It is to be understood that this invention is not limited to the specific materials, devices, methods, applications, conditions or parameters described and/or shown herein, and that the terminology used herein is for the purpose of describing particular embodiments by way of example only and is not intended to be limiting of the claimed invention. The term "plurality", as used herein, means more than one. When a range of values is expressed, another embodiment includes from the one particular value and/or to the other particular value. Similarly, when values are expressed as approximations, by use of the antecedent "about," it will be understood that the particular value forms another embodiment. All ranges are inclusive and combinable.

It is to be appreciated that certain features of the invention which are, for clarity, described herein in the context of separate embodiments, may also be provided in combination in a single embodiment. Conversely, various features of the invention that are, for brevity, described in the context of a single embodiment, may also be provided separately or in any subcombination. Further reference to values stated in ranges include each and every value within that range.

The following definitions are intended to assist in understanding the present invention:

The term "biocompatible" is defined to mean the enteron sorbent polymer is capable of coming in contact with physiologic fluids, living tissues, or organisms without producing unacceptable clinical changes during the time that the enteron sorbent polymer is in contact with the physiologic fluids, living tissues, or organisms. In some embodiments, it is intended that the enteron sorbent polymer is tolerated by the gut and alimentary canal of the organism. The enteron sorbent polymers of the present invention are preferably non-toxic. A biocompatible sorbent may be a non-biodegradable, biodegradable, or resorbable polymer.

As used herein, the term "enteron sorbent polymer" includes adenteron sorbent polymers and abenteron sorbent polymers.

The coating/dispersant on the porous ST/DVB copolymer resin can imbue the material with improved biocompatibility.

Some preferred enteron sorbent polymers comprise residues from one or more monomers or containing monomers or mixtures thereof selected from divinylbenzene and ethylvinylbezene, styrene, ethylstyrene, acrylonitrile, butyl methacrylate, octyl methacrylate, butyl acrylate, octyl acrylate, cetyl methacrylate, cetyl acrylate, ethyl methacrylate, ethyl acrylate, vinyltoluene, vinylnaphthalene, vinylbenzyl alcohol, vinylformamide, methyl methacrylate, methyl acrylate, trivinylbenzene, divinylnaphthalene, trivinylcyclohexane, divinylsulfone, trimethylolpropane trimethacrylate, trimethylolpropane dimethacrylate, trimethylolpropane triacrylate, trimethylolpropane diacrylate, pentaerythritol dimethacrylate, pentaerythritol trimethacrylate, pentaerythritol tetramethacrylate, pentaerythritol diacrylate, pentaerythritol triacrylate, pentaerythritol tetraacrylate, dipentaerythritol dimethacrylate, dipentaerythritol trimethacrylate, dipentaerythritol tetramethacrylate, dipentaerythritol diacrylate, dipentaerythritol triacrylate, dipentaerythritol tetraacrylate, and divinylformamide.

In some embodiments, the enteron sorbent polymer is a coated polymer comprising at least one crosslinking agent and at least one dispersing agent. The dispersing agent may be biocompatible. The dispersing agents can be selected from chemicals, compounds or materials such as hydroxyethyl cellulose, hydroxypopyl cellulose, poly(hydroxyethyl methacrylate), poly(hydroxyethyl acrylate), poly(hydroxypropyl methacrylate), poly(hydroxypropyl acrylate), poly(dimethylaminoethyl methacrylate), poly(dimethylaminoethyl acrylate), poly(diethylamimoethyl methacrylate), poly(diethylaminoethyl acrylate), poly(vinyl alcohol), poly(N-vinylpyrrolidinone), salts of poly(methacrylic acid), and salts of poly(acrylic acid) and mixtures thereof; the cross-linking agent selected from a group comprising divinylbenzene, trivinylbenzene, divinylnaphthalene, trivinylcyclohexane, divinylsulfone, trimethylolpropane trimethacrylate, trimethylolpropane dimethacrylate, trimethylolpropane triacrylate, trimethylolpropane diacrylate, pentaerythrital dimethacrylates, pentaerythrital trimethacrylates, pentaerythrital, tetramethacrylates, pentaerythritol diacrylates, pentaerythritol triacrylates, pentaerythritol tetraacrylates, dipentaerythritol dimethacrylates, dipentaerythritol trimethacrylates, dipentaerythritol tetramethacrylates, dipentaerythritol diacrylates, dipentaerythritol triacrylates, dipentaerythritol tetraacrylates, divinylformamide and mixtures thereof. Preferably, the enteron sorbent polymer is developed simultaneously with the formation of the coating, wherein the dispersing agent is chemically bound to the surface of the enteron sorbent polymer.

Some embodiments of the invention use an organic solvent and/or polymeric porogen as the porogen or pore-former, and the resulting phase separation induced during polymerization yield porous polymers. Some preferred porogens are benzyl alcohol, cyclohexane, cyclohexanol, cyclohexanol/toluene mixtures, cyclohexanone, decane, decane/toluene mixtures, di-2-ethylhexylphosphoric acid, di-2-ethylhexyl phthalate, 2-ethyl-1-hexanoic acid, 2-ethyl-1-hexanol, 2-ethyl-1-hexanol/n-heptane mixtures, 2-ethyl-1-hexanol/toluene mixtures, isoamyl alcohol, n-heptane, n-heptane/ethylacetate, n-heptane/isoamyl acetate, n-heptane/tetraline mixtures, n-heptane/toluene mixtures, n-hexane/toluene mixtures, pentanol, poly(styrene-co-methyl methacrylate)/dibutyl phthalate, polystyrene/2-ethyl-1-hexanol mixtures, polystyrene/dibutyl phthalate, polystyrene/n-hexane mixtures, polystyrene/toluene mixtures, toluene, tri-n-butylphosphate, 1,2,3-trichloropropane/2-ethyl-1-hexanol mixtures, 2,2,4-trimethyl pentane (isooctane), trimethyl pentane/toluene mixtures, poly(propylene glycol)/toluene mixtures poly(propylene glycol)/cyclohexanol mixtures, and poly(propylene glycol)/2-ethyl-1-hexanol mixtures.

Detailed embodiments of the present invention are disclosed herein; it is to be understood that the disclosed embodiments are merely exemplary of the invention that may be embodied in various forms. Therefore, specific structural and functional details disclosed herein are not to be interpreted as limits, but merely as a basis for teaching one skilled in the art to employ the present invention. The specific examples below will enable the invention to be better understood. However, they are given merely by way of guidance and do not imply any limitation.

The present biocompatible sorbent compositions are comprised of a plurality of pores. The biocompatible enteron sorbent polymers are designed to adsorb a broad range of toxins from less than 1 kDa to 1,000 kDa. While not intending to be bound by theory, it is believed the enteron sorbent polymer acts by sequestering molecules of a predetermined molecular weight within the pores. The size of a molecule that can be adsorbed by the enteron sorbent polymer will increase as the pore size of the enteron sorbent polymer increases. Conversely, as the pore size is increased beyond the optimum pore size for adsorption of a given molecule, adsorption of said protein may or will decrease.

The enteron sorbent polymers used in the instant invention preferably have a biocompatible exterior surface coatings but are not absolutely necessary, especially in certain circumstances, such as oral or rectal administration. Certain of these coatings are covalently bound to the enteron sorbent polymer particle (beads, for example) by free-radical grafting. The free-radical grafting may occur, for example, during the transformation of the monomer droplets into polymer beads. The dispersant coating and stabilizing the monomer droplets becomes covalently bound to the droplet surface as the monomers within the droplets polymerize and are converted into polymer. Biocompatible exterior surface coatings can be covalently grafted onto the preformed polymer beads if the dispersant used in the suspension polymerization is not one that imparts biocompatibility. Grafting of biocompatible coatings onto preformed polymer beads is carried out by activating free-radical initiators in the presence of either the monomers or low molecular weight oligomers of the enteron sorbent polymers that impart biocompatibility to the surface coating.

EXAMPLES

Example 1: Enteron Sorbent Polymer Synthesis

Reactor Setup: A jacketed kettle (5 L) is fitted with an overhead stirrer, baffle, multi-level stirrer blade, water cooled condenser, thermocouple, bubbler and gaskets (where appropriate). All unused ports are capped with the appropriate plug. Temperature is controlled with a heating/cooling unit with the temperature controller fitted with the above thermocouple.

Polymerization: Polyvinyl alcohol (PVA) is dispersed in a water charge at room temperature (RT) and then heated to 70° C. The remaining salts (See Table 1, MSP, DSP, TSP, & Sodium Nitrite) are then dissolved in the water charge. The PVA and salts solutions are heated to 80° C. with stirring. The pre-mixed organic phase including the initiator is poured into the reactor onto the aqueous phase with the stirring speed set at the rpm for formation of the appropriate droplet size. Once temperature reaches 80° C. start reaction timer (16 hours).

TABLE 1

| Item | Charge, g |
|---|---|
| Aqueous Phase Charges | |
| Ultrapure Water | 1734.47 |
| Polyvinyl Alcohol (PVA) | 5.06 |
| Monosodium Phosphate (MSP) | 5.34 |
| Disodium Phosphate (DSP) | 17.71 |
| Trisodium Phosphate (TSP) | 10.99 |
| Sodium Nitrite | 0.05 |
| Total | 1773.63 |
| Organic Phase Charges | |
| Divinylbenzene (DVB) (63%, Deltech Corp.) | 592.92 |
| Toluene | 390.48 |
| Isooctane | 448.47 |
| Benzoyl Peroxide (BPO) (97%) | 4.49 |
| Total, w/o BPO | 1431.87 |

Work-up Mark solvent level. After cooling the solvent is siphoned out to bead level. Reactor is filled to mark with Room Temperature (RT) water and heated to 50° C. to 70° C. and stirred for 30 minutes, allowed to settle for 3 to 5 minutes and then siphoned out to bead level. Beads are washed 5 times in this manner. The enteron sorbent polymer is steam stripped 6 hours and then dried in an oven overnight (~100° C.). This process results in a clean, dry porous sorbent in the form of spherical, divinylbenzene porous polymer beads. The beads were rewet with 70% IPA and the IPA exchanged with water for further reactions under aqueous conditions.

Example 2

Reactor Setup. A 5 L kettle reactor was fitted with an over-head stirrer, baffle, a water cooled condenser, a multi-level stirrer blade, a thermocouple, and a bubbler. A gasket was installed between the top lid and bottom kettle. All unused ports were capped with the appropriate plug. Temperature was controlled with a heating mantle which was regulated by a temperature controller fitted with the above-mentioned thermocouple.

Polymerization. Polyvinyl alcohol ("PVA") was dispersed in one half of the water charge at room temperature (RT) and then heated to 70° C. The remaining salts (See Table 2, MSP, DSP, TSP, & Sodium Nitrite) were then dissolved in the remainder of the water charge. The PVA and salts solutions were added to the reactor and heated to 87° C. with stirring. The pre-mixed organic phase, including the initiator, was poured into the reactor onto the aqueous phase with the stirring speed set at the revolutions per minute ("rpm") for formation of appropriate droplet size (CY12030, 480 rpm). Once the temperature reached 87° C. the reaction timer was set for 16 hours and started and the reaction was allowed to proceed.

TABLE 2

| Item | Charge, g |
|---|---|
| Aqueous Phase Charges | |
| Ultrapure Water | 1734.47 |
| Polyvinyl Alcohol (PVA) | 5.06 |
| Monosodium Phosphate (MSP) | 5.34 |
| Disodium Phosphate (DSP) | 17.71 |
| Trisodium Phosphate (TSP) | 10.99 |
| Sodium Nitrite | 0.05 |
| Total | 1773.62 |
| Organice Phase Charges | |
| Divinylbenzene (DVB)(63%) | 581.23 |
| Cyclohexanol | 1057.01 |
| Benzoyl Peroxide (BPO)(97%) | 5.91 |
| Total, w/o BPO | 1638.24 |

Work-up, Mark Solvent Level. After cooling, the solvent was siphoned out to the bead level. The reactor was filled to the mark with (RT) water and heated to between 50° C. to 70° C. and stirred for 30 minutes. Then it was allowed to settle for 3 to 5 minutes and then the liquid was siphoned out to bead level. The beads were washed five times in this manner. The reactor was then filled to the mark with RT methanol and stirred at RT for 5 minutes. Beads were allowed to settle for 3 to 5 minutes. Beads were washed 3 times in the manner. The enteron sorbent polymer was extracted via a soxhlet apparatus with acetone overnight. The enteron sorbent polymer was steam stripped for 8 hours and then dried in an oven overnight at approximately 100° C. This process resulted in a clean, dry porous adsorbent in the form of spherical, porous polymer beads. This material is called CY12001.

Modification Reaction. For charges see Table 3. Polymer was washed 10 times with isopropyl alcohol at approximately 1 bed volume per hour and then 10 times with purified water at approximately 1 bed volume per hour. The enteron sorbent polymer was sieved to the desired particle size (CY12030, −106/+45 micron) and added to the reactor setup. Excess water was siphoned to just above bed level and the charged water was then added. The temperature controller was set to 40° C. and then started. The overhead stirrer was started as well. Each reagent was added while the system was ramping up to the 40° C. set point. Ammonium Persulfate (AMPS) in water was added when the temperature was between 30° C. to 34° C. NNNN-Tetramethylethylenediamine (TMED) and water were added between 35° C. and 36° C. Vinylpyrrolidinone (VP) and water were added between 39° C. and 40° C. The two hour reaction timer was started when the temperature reached 40° C.; the reaction was allowed to proceed. After cooling, the solvent was siphoned out to the bead level. The beads were then washed 3 times with RT water at a rate of 1 bed volume per half hour. The beads were steam stripped for 6 hours. The beads were rewet in isopropyl alcohol and washed ten times in purified $H_2O$. The enteron sorbent polymer was then dried in an oven at 100° C.

This process resulted in a clean, dry adsorbent in the form of spherical, porous polymer beads. This material is called CY14149.

TABLE 3

| Modification of | CY12030 (−106/+45) | CY12001 |
|---|---|---|
| Amount of Polymer being modified, mL | 2000 | 600 |
| Charged Water, mL | 721 | 216 |
| Ammonium Persulfate (AMPS), g | 11.4 | 4.1 |
| in Water for Addition, mL | 111 | 33 |
| NNNN-Tetramethylethylenediamine (TMED), g | 12.1 | 4.3 |
| in Water for Addition, mL | 55 | 17 |
| Vinylpyrrolidinone (VP), g | 5.9 | 2.1 |
| in Water for Addition, mL | 166 | 50 |
| Polymer Designation | CY14149 | CY12031 |

Example 3: Pore Structure Characterization

The pore structures of the enteron sorbent polymers are analyzed with a either Micromeritics AutoPore IV 9500 V1.09 a Mercury Penetrometer (Hg Intrusion instrument) or a Micromeritics ASAP 2010 instrument (N2 Desorbtion). See FIGS. 1-4.

TABLE 4

Pore volume data for CY12030 measured by Nitrogen Desorption.

| Pore Diameter Range | Pore Volume (cc/g) |
|---|---|
| 10 Å to 250,000 Å | 1.6545 |
| 50 Å to 250,000 Å | 1.4292 |
| 250 Å to 250,000 Å | 0.9504 |
| 300 Å to 250,000 Å | 0.8380 |
| 500 Å to 250,000 Å | 0.2352 |
| 1,000 Å to 250,000 Å | 0.0088 |
| 10,000 Å to 250,000 Å | 0 |

TABLE 5

Pore volume data for CY12031 measured by Mercury Intrusion.

| Pore Diameter Range | Pore Volume (cc/g) |
|---|---|
| 10 Å to 250,000 Å | 2.4016 |
| 50 Å to 250,000 Å | 2.4016 |
| 250 Å to 250,000 Å | 2.4052 |
| 300 Å to 250,000 Å | 1.9828 |
| 500 Å to 250,000 Å | 1.7602 |
| 1,000 Å to 250,000 Å | 1.4103 |
| 10,000 Å to 250,000 Å | 0.3297 |

Additional Examples and Illustrative Embodiments

Exposure to ionizing radiation results in Acute Radiation Syndrome (ARS). Epistem have experience investigating the effects on the gastrointestinal syndrome (GI-ARS), which occurs at doses of radiation generally above 12 Gy (depending on the conditions/mouse strain/size etc). GI-ARS typically results in severe weight loss, diarrhea and eventually morbidity within 10 days of irradiation. The partial-body irradiation (PBI) model was used in this study. A level of 5% bone marrow sparing was selected (PBI BM5) where the lower hind limbs (tibiae, fibulae and feet) were lead shielded during irradiation. PBI models (2.5-5% shielding) are considered reality models for accidental or terrorist induced exposure i.e. in such cases it is likely that a small amount of bone marrow will be shielded in some way. The model also has the benefit of allowing some mice to survive long enough to enter hematological syndrome (H-ARS) and so ultimately could be used to evaluate mitigators of both syndromes.

In the current study the efficacy of a 50% slurry of enteron sorbent polymer was evaluated to determine the effect on survival time of C57BL/6 mice post-high dose radiation. An $LD50_{10}$ radiation dose of 13.5 Gy was selected. This is a dose that causes 50% lethality by day 10 in undosed animals.

Aim:

To determine the efficacy of a 50% slurry of enteron sorbent polymer to increase survival time of C57BL/6 mice following high dose (13.5 Gy) partial body irradiation.

Methods:

40 male 8-10 week old C57BL/6 mice were purchased and then randomised into 2 groups of 20. After acclimatising for 2 weeks they were exposed to 13.5 Gy partial-body irradiation, using a 300 kV X-ray source, shielding approximately 5% of the bone marrow (tibiae, fibulae and feet of both lower limbs). Mice were then orally gavaged twice daily with 0.15 mL water or 0.15 mL 50% slurry of an enteron sorbent polymer starting from 24 hours post-irradiation. Immediately following administration a further 0.15 mL of water was gavaged to all mice to aid transit of the treatment (slurry) administration. Dosing volumes remained constant throughout the study. Animal survival, weights and incidence of diarrhea were tracked throughout the study for 15 days.

Results:

After irradiation there was, as may be expected, a rapid weight loss. Group means then plateau followed by weight recovery in the surviving mice. The group receiving an enteron sorbent polymer lost less weight than the vehicle group, with the maximum weight lost being approximately 5% less in the enteron sorbent polymer treated group. Further, the time to reach 25% weight loss (a frequent fixed criteria for euthanasia) was increased by 2 days in the enteron sorbent polymer group. The median time to 25% weight loss was 7.5 days compared to 5.5 days in the vehicle group and was statistically significant (p=0.03).

The radiation dose selected was estimated to deliver an $LD50_{10}$ but actually achieved an $LD85_{10}$. This increased mortality is likely to be a result of the extra handling/stresses associated with the oral administrations (the $LD50_{10}$ is based on a radiation survival curve in untreated mice). Administration of an enteron sorbent polymer improved survival during the period of GI-ARS (i.e. up to day 10) shifting the mean and median survival time by 1 day. However, this was not statistically significant (p=0.1045). The difference between the groups in the proportion of animals alive was greatest days 7-9 i.e. during the period of GI-ARS; in particular by day 8 the proportion of animals alive was 85% for the enteron sorbent polymer group and 55% for the vehicle group. However, this difference did not quite reach statistical significance (p=0.0824).

Upon examination of both small intestine and colon of the treated mice euthanized on days 7-9 no trace of remaining enteron sorbent polymer beads was observed. The sum of the diarrhea scores per group were skewed a little by one very sick animal in the control group, but were 43 in the vehicle group (30 if the one extreme mouse is omitted) and 14 in the enteron sorbent polymer group. Group mean scores were 2.1 (1.6 if the extreme mouse omitted) in the vehicle group and 0.7 in the enteron sorbent polymer group. Fourteen mice in the vehicle group experienced diarrhea, compared to 8 in the enteron sorbent polymer group. Within these animals there were 35 observed incidents in the vehicle group (28 if the extreme mouse is omitted) and 12 in the enteron sorbent polymer group. These comprised of 27 mild and 8 severe cases in the vehicle group (26 and 2 if the extreme mouse is omitted) and 10 mild and 2 severe in the enteron sorbent polymer group. Statistical analysis confirmed that the maximum score and average score were less in the enteron sorbent polymer group. Furthermore the mean proportion of time periods with diarrhea was around 7% in the enteron sorbent polymer group compared to around 22% in the vehicle group. The difference between the treatments was not quite statistically significant for the maximum score and average score (p=0.08 and 0.06 respectively). However the difference between the treatments in the proportion of time periods with diarrhea was statistically significant (p=0.02).

Conclusion:

In this initial proof of concept study an enteron sorbent polymer showed efficacy in the high dose partial body irradiation model during the GI-ARS timeframe. Survival time was increased, presumably directly related to the reduced weight loss following enteron sorbent polymer treatment, and diarrhea severity and duration were also reduced. Whilst all of these did not achieve statistical significance, and the level of mortality observed was higher than that observed in non-gavaged animals (which may impact the ability to achieve a significant improvement in animal survival numbers), the data are very encouraging and warrant further investigation into the possible use of enteron sorbent porous polymers as a GI-ARS mitigator.

2. Procedures 2.1 Animals and Caging

A total of 40 C57BL/6 male mice (Harlan Laboratories, UK) were purchased for the study. Animals were 8-10 weeks old on supply and used at 10-12 weeks of age. All mice were held in individually ventilated cages (IVCs) in an SPF (Specific Pathogen Free) barrier unit. The animals were identified by numbered cages and by ear punches. Handling of mice outside of their cages was always done in a sterile laminar flow station. A maximum of 2 cages were open at any one time.

2.2 Diet and Animal Welfare

The animals were fed a normal diet (2918x extruded diet, Harlan UK) ad libitum. Animals were maintained on acidified water from time of arrival and throughout the study. Acid water was also used to wet the food from day 4. There was a constant room temperature of 21±2° C. and a mean relative humidity of 55±10%. The day-night cycle was constant, with light and dark phases of 12 hours each (07:00 hr/19:00 hr switch). Animal health was monitored daily and cages were cleaned at regular intervals.

2.3 Radiation Parameters and Dosimetry

Based on previous studies, a dose of 13.5 Gy was selected to aim to achieve an $LD50_{10}$ dose.

Animals were irradiated at 15:00 hrs+/−1 hour. Irradiation was performed using an Xstrahl RS320 X-ray set operated at 300 kV, 10 mA. The X-ray tube has additional filtration to give a radiation quality of 2.3 mm Cu half-value layer (HVL). Mice were anaesthetised, placed in a plexiglass jig with lower hind limbs shielded and positioned at a distance of 700 mm from the focus of the X-ray tube. Partial-Body Irradiation (PBI BM5) was delivered at a dose rate of 0.812 Gy/min.

X-ray output checks during the series of irradiations were measured using an ionizing chamber placed within the mouse restraint and showed that for the intended machine dose of 13.5 Gy the actual dose delivered ranged from 13.48-13.58 and was therefore well within the 2% variation limits considered acceptable.

2.4 Preparation and Administration of Vehicle

The vehicle was sterile water and was supplied as pre-prepared aliquots.

Before dosing, air bubbles within the syringe were removed by inverting the syringe so that the bubbles rose towards the gavage needle and were then expelled, leaving 0.15 mL water.

Vehicle was administered orally (p.o.) 24-25 hours post-irradiation and then twice daily (10 hours apart) throughout the study. This volume of 0.15 mL was not adjusted throughout the study, regardless of weight loss. Immediately following each dose of vehicle a further 0.15 mL of water was administered, again by oral gavage. This volume was, again, not adjusted throughout the study.

2.5 Preparation and Administration of Enteron Sorbent Polymer

Enteron sorbent porous polymer beads were supplied as pre-prepared aliquots. Enteron sorbent porous polymer beads (Sample ID: CY14149) were supplied in seventy (70) 2 mL polypropylene tubes and stored at 4° C. upon arrival. Before dosing, the tube was inverted several times and the gavage needle placed near the bottom of the tube before drawing up the suspension in order to avoid any empty beads floating on the surface. Air bubbles within the syringe were removed by inverting the syringe so that the bubbles rose towards the gavage needle and were then expelled, leaving 0.15 mL enteron sorbent polymer.

The enteron sorbent polymer beads were administered orally (p.o. via gavage) 24-25 hours post-irradiation and then twice daily (10 hours apart) throughout the study. This volume of 0.15 mL was not adjusted throughout the study, regardless of weight loss. Immediately following each dose of vehicle a further 0.15 mL of water was administered, again by oral gavage. This volume was, again, not adjusted throughout the study.

2.6 Clinical Examinations and Weighing

Mice were weighed daily and clinical observations (diarrhea) noted daily from day 4. Mice were euthanized when moribund. Any animal demonstrating more than 15% weight loss was considered unwell and humanely euthanized if the weight loss was sustained at greater than 20% for 24 hours and mice also demonstrated signs of a moribund state (withdrawn behavior, reduced body temperature as judged by feeling cool to touch, lack of grooming and dehydration as judged by a persistent skin tent on pinching). A random selection of six moribund mice from the enteron sorbent polymer group were taken for necropsy on days 7-9 to look for the presence of test article within the intestines.

3. Results and Discussion 3.1 Weight Loss

After irradiation there was, as may be expected, a rapid weight loss. Group means then plateau followed by weight recovery in the surviving mice. The group receiving enteron sorbent polymer lost less weight than the vehicle group with the maximum weight lost being approximately 5% less in the enteron sorbent polymer treated group.

Figure 5:
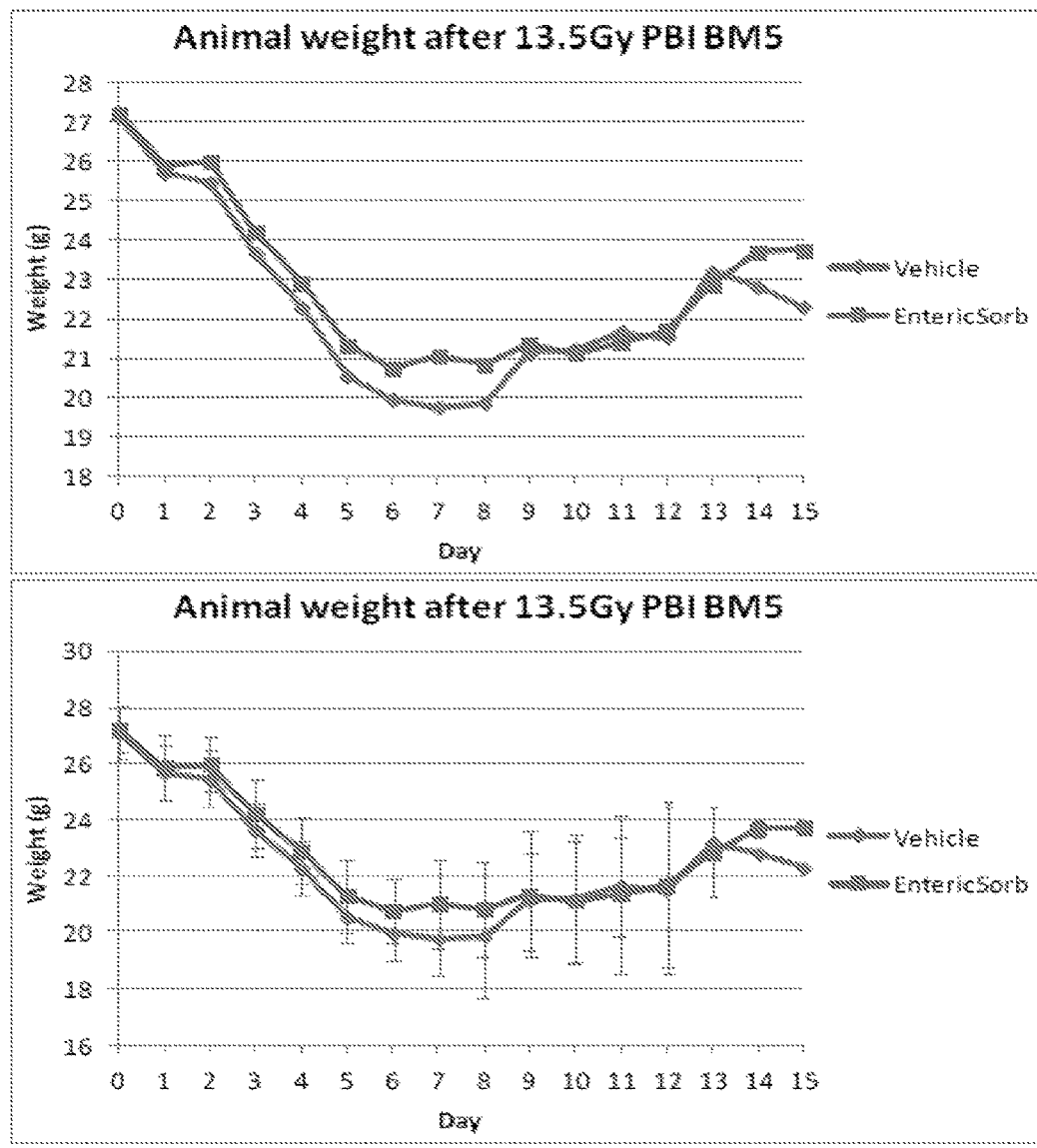
FIG. 5 shows a change in group mean body weight. C57BL/6 mice were irradiated, 20 per group, with 13.5 Gy partial-body irradiation (with 5% of bone marrow shielded). Mice were treated with either 150 µL of water (control) or 150 µL of 50% enteron sorbent polymer slurry (treatment) twice a day for 15 days post 24-hour exposure. A second gavage with sterile water was administered to both control and treated groups immediately following the first gavage for extra hydration and/or wash down of beads from the first gavage. The mean weights of the surviving mice are plotted (top) along with the same plots showing Standard Deviation (bottom)
Figure 6:
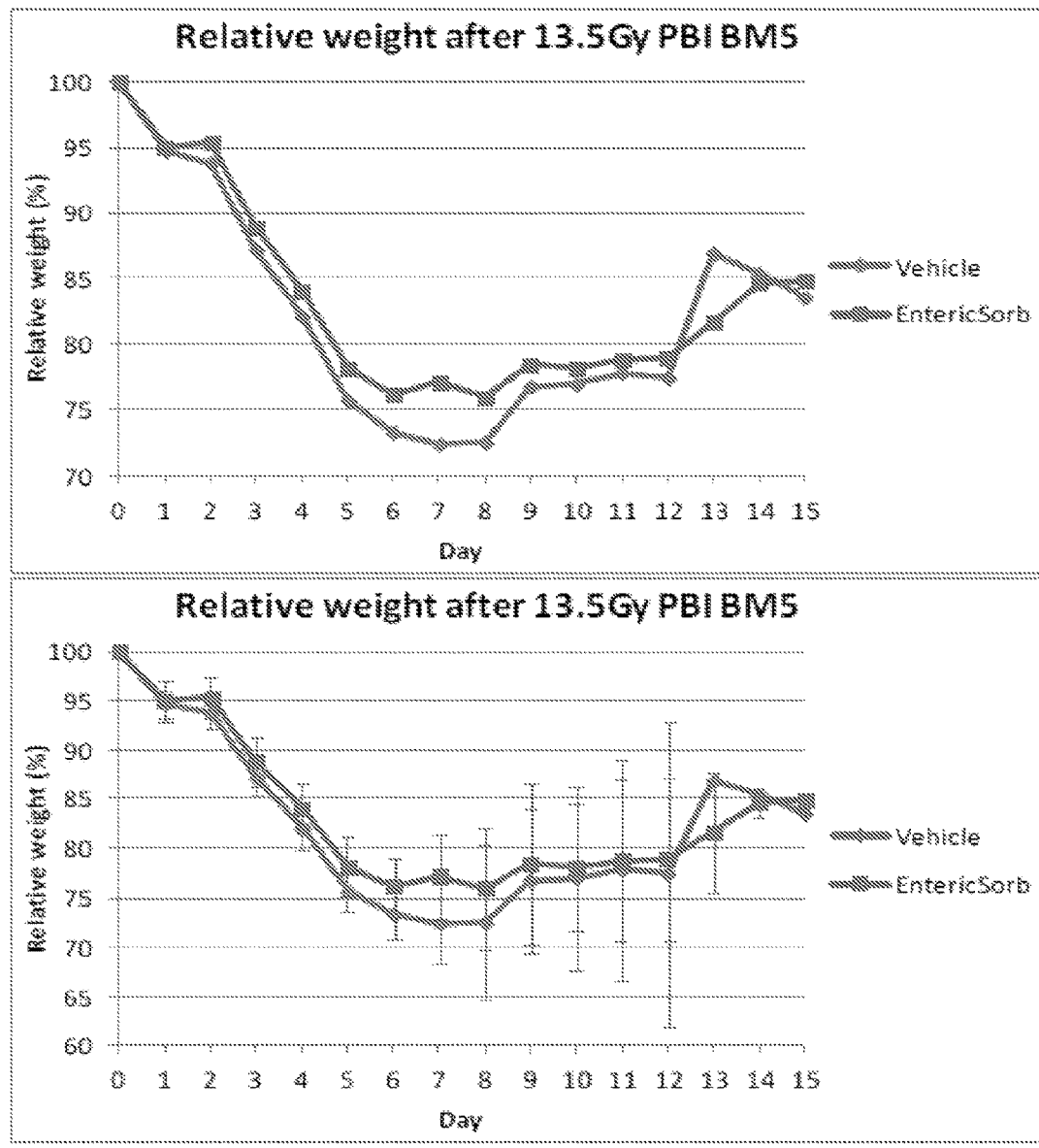
FIG. 6 shows a change in relative body weight. C57BL/6 mice were irradiated, 20 per group, with 13.5 Gy partial-body irradiation (with 5% of bone marrow shielded). Mice were dosed with either 150 µL of water (control) or 150 µL of 50% enteron sorbent polymer slurry (treatment) twice a day for 15 days. A second gavage with sterile water was administered to both control and treated groups immediately following the first gavage for extra hydration and/or wash down of beads from the first gavage. The weights of the surviving mice are plotted as a percentage of the weight at the time of irradiation on day 0 (top) along with the same plots showing Standard Deviation (bottom)

The weights and relative weights, plotted as a percentage of the weight on day 0, are shown in FIGS. 5 and 6.

Figure 7:
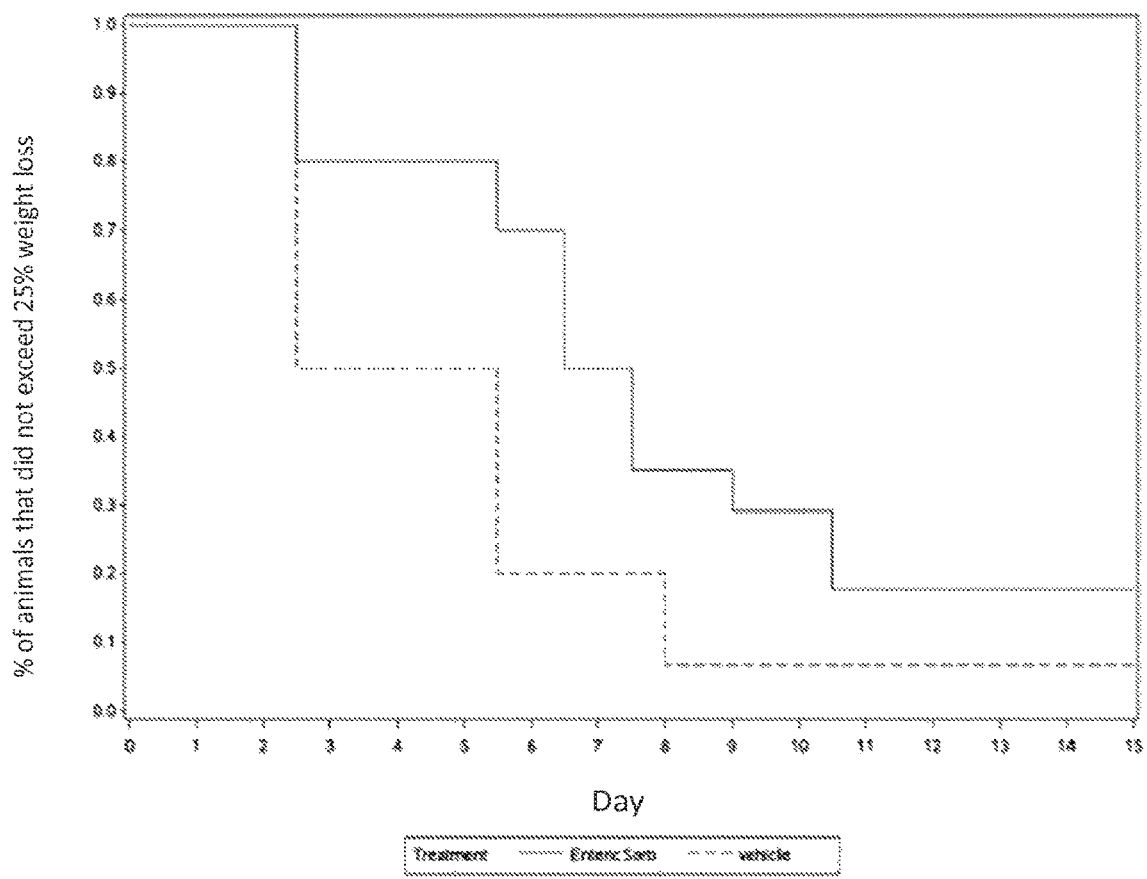
FIG. 7 illustrates the percentage of control versus treated animals (Y-axis) that are still above a 25% weight loss threshold as a function of time (days). At 25% weight loss, animals were sacrificed.

The number of days until the weight was reduced by at least 25% from day 0 was analysed in a similar manner as the time to death (see below). 25% weight loss is the level often used as euthanasia criteria, and therefore would be reflective of an animal survival plot by many. At Epistem it is combined with other signs of distress, since from extensive experience it is known that animals often recover from this level of weight loss post irradiation. Animals that did not lose more than 25% of their body weight were plotted by treatment group versus control (FIG. 7) and the times to 25% weight loss summarized (Table 1). This showed the time to 25% weight loss to be increased by 2 days in the enteron sorbent polymer group. The median time to 25% weight loss was 7.5 days compared to 5.5 days in the vehicle group. This difference was statistically significant (p=0.03; log-rank test).

TABLE 1

Estimates of Time to 25% Weight Loss by Treatment

| Treatment | Median | 95% Lower CL | 95% Upper CL | Mean | Std. Err. |
|---|---|---|---|---|---|
| EntericSorb | 7.5 | 6.0 | 10.0 | 8.0* | 0.53 |
| Vehicle | 5.5 | 5.0 | 6.0 | 6.3* | 0.44 |

NE = Not estimable,
*Biased estimate 3.2 Animal Survival

The dose of radiation selected was based on previous estimates of the LD50 dose in undosed mice. The dose response curve is very steep and so the probability of a study delivering exactly these levels of survival is low. The twice daily oral gavages employed in the current study are likely to have further influenced the level of lethality—since, whilst the water will hydrate the mice, the increased handling and dosing stresses, (particularly in sick mice) may well increase mortality.

Figure 8:
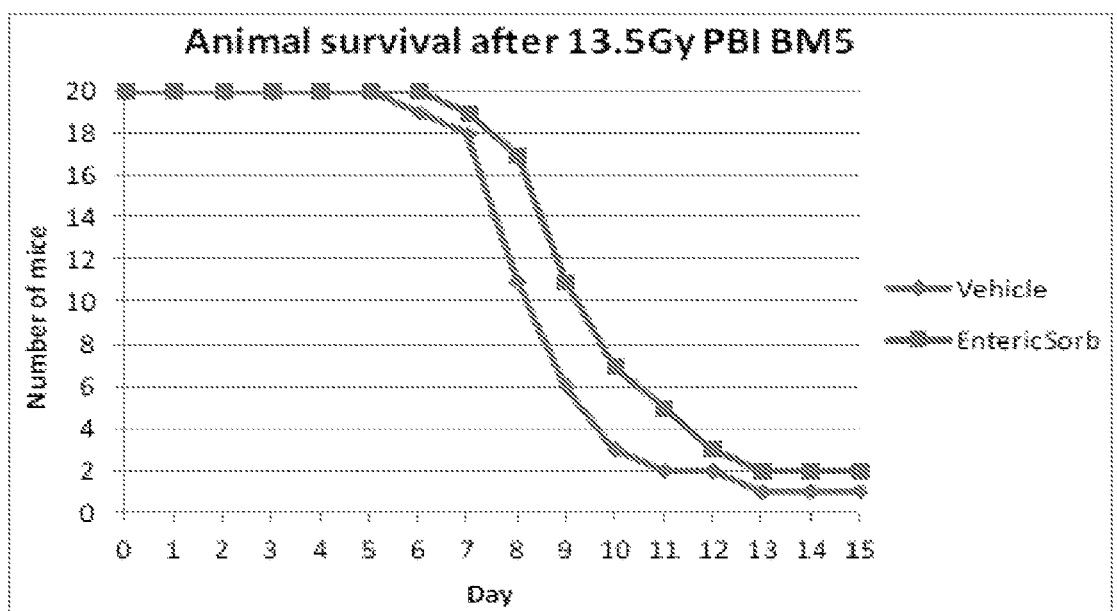
FIG. 8: illustrates animal survival following partial-body irradiation, with 5% of bone marrow shielded. Twenty C57BL/6 mice per group were irradiated and maintained on acidified water. Mice were dosed with either 150 µL of water (control) or 150 µL of 50% enteron sorbent polymer slurry (treatment) twice a day for 15 days post 24-hour exposure. A second gavage with sterile water was administered to both control and treated groups immediately following the first gavage for extra hydration and/or wash down of beads from the first gavage. Mice were checked daily and euthanized when moribund or when they exceeded 25% weight loss from baseline.

The levels of survival in the irradiated mice are plotted in FIG. 8 and illustrate that the dose estimated to deliver an $LD50_{10}$ actually achieved an $LD85_{10}$. All except one mouse was euthanized—the one being found dead in the vehicle group (mouse 18).

Figure 9:
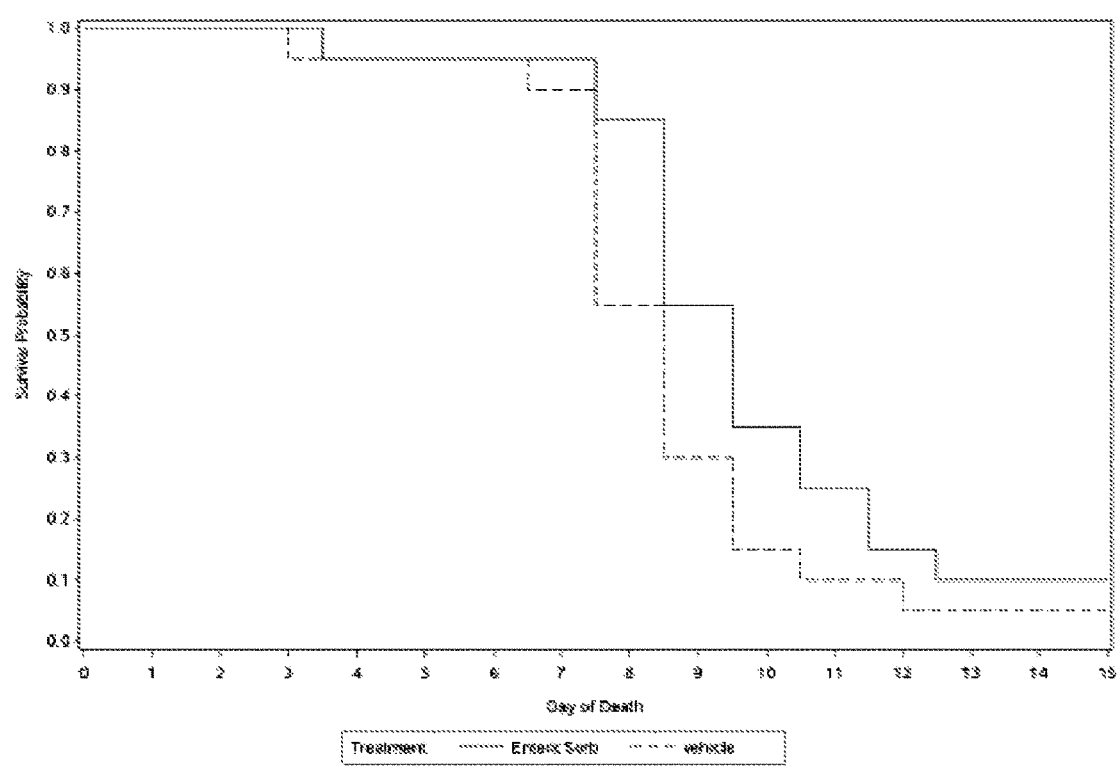
FIG. 9: depicts Kaplan-Meier survival curves of the time to death in the control and treatment populations.

Kaplan-Meier survival curves of the time to death were plotted by treatment group (FIG. 9) and the survival times summarized (Table 2). This showed the time to death to be slightly increased in the enteron sorbent polymer group. Both the mean and median time to death was 10 days compared to 9 days in the vehicle group. However this difference was not statistically significant (p=0.11; log-rank test).

TABLE 2

Estimates of Time to Death by Treatment

| Treatment | Median | 95% Lower CL | 95% Upper CL | Mean | Std. Err. |
|---|---|---|---|---|---|
| EntericSorb | 710.0 | 9.0 | 11.0 | 10.1* | 0.40 |
| Vehicle | 9.0 | 8.0 | 10.0 | 9.1* | 0.39 |

NE = Not estimable,
*Biased estimate

The difference between the groups in the proportion of animals still alive appeared greatest at around days 7-9 i.e. during the period of GI-ARS; in particular by day 8 the proportion of animals alive was 85% for the enteron sorbent polymer group and 55% for the vehicle group. However, this difference did not quite reach statistical significance (p=0.08; Fisher's exact test).

Upon examination of both small intestine and colon of the treated mice euthanized on days 7-9 no trace of enteron sorbent polymer beads were observed.

3.3 Diarrhea

Figure 10:
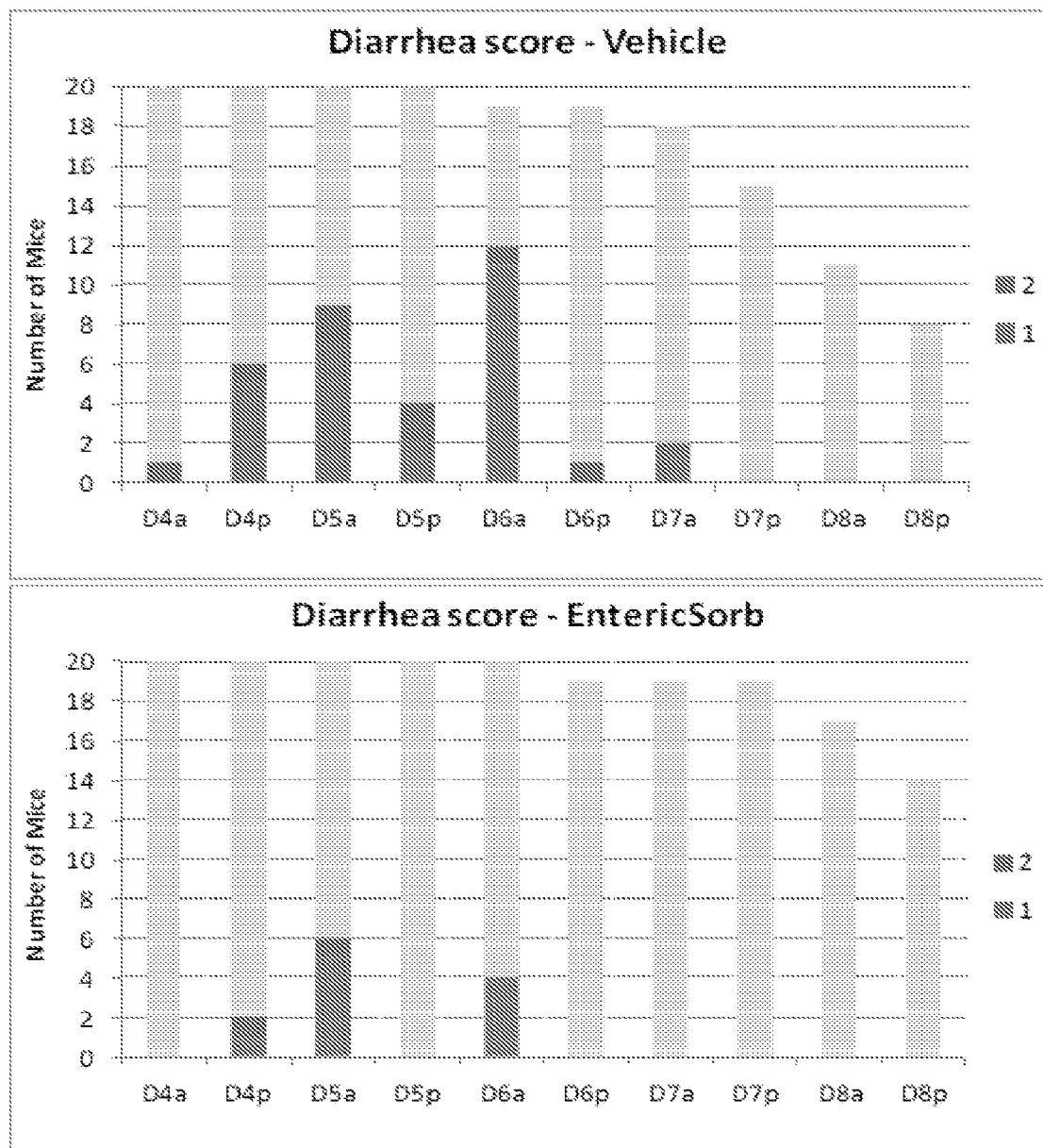
FIG. 10: presents data for animal diarrhea post-13.5 Gy partial-body irradiation (with 5% of bone marrow shielded) (vehicle top, enteron sorbent polymer bottom). The plots illustrate the number of mice exhibiting diarrhea of a score 1 (mild) or 2 (severe) from days 4-8 (am and pm observations indicated by D4a, D4p, D5a, D5p etc.). Grey bars indicate the number of mice remaining in the study.

Diarrhea was observed from day 4 and graded (where 0 was normal stool consistency, 1 was loose stools, 2 was severe overt diarrhea; a score of 3 is liquid faeces with extended pen-anal/tail soilage). The data is tabulated in the Appendix and plotted in FIG. 10 below.

The sum of the diarrhea scores per group are skewed a little by one very sick animal in the control group, but were 43 in the vehicle group (30 if the one extreme mouse is omitted) and 14 in the enteron sorbent polymer group. Group mean scores were 2.1 (1.6 if the extreme mouse omitted) in the vehicle group and 0.7 in the enteron sorbent polymer group.

Fourteen mice in the vehicle group experienced diarrhea, compared to 8 in the enteron sorbent polymer group. Within these animals there were 35 observed incidents in the vehicle group (28 if the extreme mouse is omitted) and 12 in the enteron sorbent polymer group. These comprised of 27 mild and 8 severe cases in the vehicle group (26 and 2 if the extreme mouse is omitted) and 10 mild and 2 severe in the enteron sorbent polymer group.

For further statistical analysis the daily diarrhea scores were used to derive three summary measures for each animal: the maximum diarrhea score, the average diarrhea score and the proportion of time periods (in this case half-days) for which diarrhea was present (i.e., had a score>0). These summary measures were summarized by treatment group (Table 3) and the treatment groups compared using a t-test. This showed that the maximum score and average score were less in the enteron sorbent polymer group. Furthermore the mean proportion of time periods with diarrhea was around 7% in the enteron sorbent polymer group compared to around 22% in the vehicle group.

The difference between the treatments was not quite statistically significant for the maximum score and average score (p=0.08 and 0.06 respectively). However the difference between the treatments in the proportion of time periods with diarrhea was statistically significant (p=0.02).

TABLE 3

Diarrhea Summary Measures by Treatment

| Treatment | Label | N | Mean | Std Dev | Median | Min | Max |
|---|---|---|---|---|---|---|---|
| EntericSorb | Maximum score | 20 | 0.45 | 0.60 | 0.00 | 0.00 | 2.0 |
|  | Average score | 20 | 0.08 | 0.15 | 0.00 | 0.00 | 0.56 |
|  | Proportion of half-days with diarrhea | 20 | 6.78 | 11.44 | 0.00 | 0.00 | 40.0 |
|  | Maximum score | 20 | 0.80 | 0.82 | 1.0 | 0.00 | 2.00 |
|  | Average score | 20 | 0.27 | 0.42 | 0.19 | 0.00 | 1.86 |
|  | Proportion of half-days with diarrhea | 20 | 22.07 | 24.72 | 18.75 | 0.00 | 100.00 |

4. Conclusion

In this initial proof of concept study enteron sorbent polymer showed efficacy in the high dose partial-body irradiation model during the GI-ARS timeframe. Survival time was increased, presumably directly related to the reduced weight loss following enteron sorbent polymer treatment, and diarrhea severity and duration were also reduced. These data demonstrate a statistical trend to benefit and are very encouraging and warrant further investigation into the possible use of enteron sorbent polymers as GI-ARS mitigators or protectants.

There are a variety of options for further studies, each with aim of demonstrating increased efficacy, predominantly on animal survival number at a given timepoint (the actual timepoint may be defined as an appropriate time during GI-ARS—typically day 6-8 in a TBI model, extending towards day 10 in a PBI BM5 model). Thus, a statistically significant increase from a given LD (e.g. LD50) on day 8 (defined $LD50_8$) should be demonstrated. In a TBI model of GI-ARS all animals will ultimately die, even if mitigated somewhat, due to H-ARS. Thus, the PBI model is designed such that animals that survive the early stage GI-ARS will maintain sufficient bone marrow function to also survive the later stage H-ARS. Either is an appropriate and acceptable model for demonstrating efficacy during the GI-ARS timeframe.

In order to increase efficacy options include:

1. Reducing the number or duration of gavage administrations (assuming that this is increasing mortality due to handling stresses in sick mice). The severity of the handling stress may be offset a little by the rehydration effects, and so both need to be considered.

2. Reducing the radiation dose (remaining within the GI toxicity range but accepting that a lower dose may be closer to an LD50$_{8-10}$ and less of a challenge for any prospective mitigator to 'rescue'). Clearly the animal survival dose response curve is unknown for this administration schedule, but we do know that the LD curve is steep, and so a small reduction to 13 Gy may be sufficient.

3. Moving from a PBI to a TBI model—generally tougher to rescue but enteron sorbent polymer beads may behave differently in this model, given the lack of immunological competence (bone marrow survival) and increased risk of septicaemia. The profile of sequestration of both cytokines and bacterial toxins may be different.

Ultimately, once further efficacy is demonstrated, confirmation of the mechanism of action will be needed (demonstration of improved histopathology, reduction in bacterial toxins, demonstration of improved cytokine profile etc).

5.1 Animal Weights

| Treatment | Mouse Number | Day 0 | Day 1 | Day 2 | Day 3 | Day 4 | Day 5 | Day 6 | Day 7 | Day 8 | Day 9 | Day 10 | Day 11 | Day 12 | Day 13 | Day 14 | Day 15 |
|---|---|---|---|---|---|---|---|---|---|---|---|---|---|---|---|---|---|
| 13.5Gy PBI BM5 Vehicle | 1 | 27.3 | 26.1 | 25.6 | 23.8 | 23.3 | 21.9 | 20.9 | 20.9 | | | | | | | | |
| | 2 | 27.1 | 25.4 | 25.1 | 23.7 | 22.9 | 20.2 | 19.4 | 19.5 | | | | | | | | |
| | 3 | 29.2 | 28.0 | 27.7 | 25.7 | 24.4 | 22.9 | 22.0 | 22.2 | 22.4 | 22.2 | 21.3 | 20.4 | 19.4 | | | |
| | 4 | 27.1 | 26.4 | 25.9 | 24.0 | 22.5 | 20.6 | 19.6 | 18.9 | | | | | | | | |
| | 5 | 26.9 | 25.8 | 25.5 | 24.4 | 23.1 | 21.0 | 20.5 | 21.0 | 22.5 | 22.6 | 18.9 | | | | | |
| | 6 | 26.3 | 24.5 | 24.4 | 22.6 | 21.7 | 19.6 | 19.0 | 18.8 | 18.8 | | | | | | | |
| | 7 | 27.4 | 26.6 | 26.5 | 24.7 | 23.1 | 21.0 | 20.1 | 18.5 | | | | | | | | |
| | 8 | 26.7 | 25.4 | 25.2 | 23.5 | 22.7 | 21.3 | 21.3 | 22.0 | 23.5 | 23.1 | 23.4 | 22.9 | 23.6 | 23.2 | 22.8 | 22.3 |
| | 9 | 26.7 | 25.3 | 24.7 | 23.2 | 22.1 | 20.1 | 19.5 | 19.5 | 17.9 | | | | | | | |
| | 10 | 28.3 | 26.4 | 25.9 | 24.1 | 22.5 | 20.7 | 19.9 | 20.5 | 19.7 | | | | | | | |
| | 11 | 26.1 | 24.7 | 23.8 | 21.7 | 20.3 | 19.3 | 18.2 | 17.8 | 16.0 | | | | | | | |
| | 12 | 28.5 | 26.8 | 27.1 | 24.6 | 23.1 | 20.8 | 20.4 | 19.9 | 18.5 | | | | | | | |
| | 13 | 26.4 | 25.3 | 25.1 | 23.4 | 21.9 | 20.1 | 19.3 | | | | | | | | | |
| | 14 | 27.4 | 25.8 | 25.5 | 23.3 | 21.4 | 20.2 | 20.0 | 20.1 | 19.4 | 18.9 | | | | | | |
| | 15 | 27.6 | 25.8 | 25.3 | 23.9 | 21.8 | 20.5 | 19.3 | 18.4 | | | | | | | | |
| | 16 | 26.6 | 24.8 | 25.2 | 23.1 | 21.6 | 19.7 | 19.7 | 19.7 | 19.9 | 20.1 | | | | | | |
| | 17 | 26.0 | 25.2 | 25.0 | 22.9 | 21.3 | 19.7 | 19.2 | 18.8 | | | | | | | | |
| | 18 | 25.5 | 24.0 | 23.8 | 22.2 | 20.8 | 19.1 | | | | | | | | | | |
| | 19 | 27.2 | 25.0 | 25.0 | 23.3 | 22.0 | 20.3 | 19.7 | 18.3 | | | | | | | | |
| | 20 | 28.5 | 26.9 | 26.9 | 25.1 | 23.0 | 21.6 | 21.0 | 20.4 | 19.7 | 19.8 | | | | | | |
| | Mean | 27.1 | 25.7 | 25.5 | 23.7 | 22.3 | 20.5 | 19.9 | 19.7 | 19.8 | 21.1 | 21.2 | 21.7 | 21.5 | 23.2 | 22.8 | 22.3 |
| | SD | 0.9 | 1.0 | 1.0 | 1.0 | 1.0 | 0.9 | 0.9 | 1.3 | 2.2 | 1.7 | 2.3 | 1.8 | 3.0 | | | |
| 13.5Gy PBI BM5 EntericSorb | 21 | 28.2 | 27.3 | 26.9 | 25.2 | 24.1 | 23.0 | 22.7 | 21.4 | 19.6 | | | | | | | |
| | 22 | 26.5 | 25.1 | 25.3 | 22.0 | 20.7 | 19.4 | 19.8 | 20.1 | 20.3 | 19.4 | 18.3 | | | | | |
| | 23 | 25.7 | 23.9 | 24.1 | 21.9 | 20.8 | 19.0 | 18.5 | 17.6 | | | | | | | | |
| | 24 | 28.2 | 27.8 | 27.7 | 26.1 | 24.8 | 23.8 | 23.3 | 23.6 | 23.2 | 21.5 | | | | | | |
| | 25 | 27.6 | 26.2 | 26.0 | 23.9 | 22.3 | 20.2 | 19.4 | | | | | | | | | |
| | 26 | 26.8 | 24.8 | 24.6 | 23.5 | 22.8 | 21.0 | 20.7 | 19.8 | 19.0 | 18.0 | | | | | | |
| | 27 | 27.7 | 25.9 | 26.0 | 25.3 | 23.9 | 22.3 | 21.2 | 20.6 | 19.5 | | | | | | | |
| | 28 | 26.8 | 25.8 | 25.4 | 24.1 | 23.3 | 21.7 | 20.5 | 21.2 | 21.1 | 21.1 | 19.0 | | | | | |
| | 29 | 27.9 | 26.6 | 26.2 | 25.0 | 24.0 | 21.7 | 21.1 | 20.6 | 19.0 | | | | | | | |
| | 30 | 27.6 | 25.1 | 25.5 | 23.7 | 23.2 | 21.7 | 20.8 | 21.2 | 20.3 | 19.7 | | | | | | |
| | 31 | 27.5 | 26.1 | 26.6 | 24.6 | 23.1 | 21.7 | 20.7 | 19.7 | 19.3 | | | | | | | |
| | 32 | 28.0 | 27.4 | 27.9 | 25.6 | 24.2 | 22.7 | 22.1 | 22.2 | 19.8 | 18.5 | | | | | | |
| | 33 | 26.8 | 25.8 | 25.9 | 23.7 | 22.5 | 21.2 | 20.9 | 22.0 | 22.6 | 22.7 | 21.0 | 18.4 | | | | |
| | 34 | 27.8 | 26.0 | 26.4 | 25.2 | 23.5 | 21.2 | 20.2 | 21.2 | 19.4 | | | | | | | |
| | 35 | 26.3 | 24.1 | 25.1 | 23.2 | 21.9 | 20.1 | 20.0 | 21.1 | 21.8 | 22.7 | 20.3 | 20.0 | | | | |
| | 36 | 27.7 | 26.0 | 26.2 | 24.6 | 22.7 | 21.5 | 20.6 | 21.5 | 20.3 | | | | | | | |
| | 37 | 28.1 | 27.0 | 26.2 | 24.8 | 23.1 | 21.7 | 21.8 | 23.7 | 24.4 | 24.8 | 24.0 | 24.6 | 22.9 | 21.7 | 23.5 | 23.7 |
| | 38 | 25.4 | 24.4 | 24.8 | 22.4 | 20.7 | 19.0 | 18.7 | 18.0 | | | | | | | | |
| | 39 | 27.9 | 27.3 | 27.1 | 25.7 | 24.2 | 22.6 | 21.4 | 22.8 | 23.5 | 24.4 | 23.9 | 24.2 | 23.9 | 24.0 | 23.9 | 23.8 |
| | 40 | 26.3 | 25.2 | 25.9 | 24.1 | 22.4 | 20.6 | 20.5 | 20.9 | 20.8 | 21.9 | 21.2 | 19.7 | 18.3 | | | |
| | Mean | 27.2 | 25.9 | 26.0 | 24.2 | 22.9 | 21.3 | 20.7 | 21.0 | 20.8 | 21.3 | 21.1 | 21.4 | 21.7 | 22.9 | 23.7 | 23.8 |
| | SD | 0.9 | 1.1 | 1.0 | 1.2 | 1.2 | 1.3 | 1.2 | 1.6 | 1.7 | 2.3 | 2.2 | 2.8 | 3.0 | 1.6 | 0.3 | 0.1 |

5.2 Animal Weights As A Percentage of 0

| Treatment | Mouse Number | Day 0 | Day 1 | Day 2 | Day 3 | Day 4 | Day 5 | Day 6 | Day 7 | Day 8 | Day 9 | Day 10 | Day 11 | Day 12 | Day 13 | Day 14 | Day 15 |
|---|---|---|---|---|---|---|---|---|---|---|---|---|---|---|---|---|---|
| 13.5Gy PBI BM5 Vehicle | 1 | 100.0 | 95.6 | 93.8 | 87.2 | 85.3 | 80.2 | 76.6 | 76.6 | | | | | | | | |
| | 2 | 100.0 | 93.7 | 92.6 | 87.5 | 84.5 | 74.5 | 71.6 | 72.0 | | | | | | | | |
| | 3 | 100.0 | 95.9 | 94.9 | 88.0 | 83.6 | 78.4 | 75.3 | 76.0 | 76.7 | 76.0 | 72.9 | 69.9 | 66.4 | | | |
| | 4 | 100.0 | 97.4 | 95.6 | 88.6 | 83.0 | 76.0 | 72.3 | 69.7 | | | | | | | | |
| | 5 | 100.0 | 95.9 | 94.8 | 90.7 | 85.9 | 78.1 | 76.2 | 78.1 | 83.6 | 84.0 | 70.3 | | | | | |
| | 6 | 100.0 | 93.2 | 92.8 | 85.9 | 82.5 | 74.5 | 72.2 | 71.5 | 71.5 | | | | | | | |
| | 7 | 100.0 | 97.1 | 96.7 | 90.1 | 84.3 | 76.6 | 73.4 | 67.5 | | | | | | | | |
| | 8 | 100.0 | 95.1 | 94.4 | 88.0 | 85.0 | 79.8 | 79.8 | 82.4 | 88.0 | 86.5 | 87.6 | 85.8 | 88.4 | 86.9 | 85.4 | 83.5 |
| | 9 | 100.0 | 94.8 | 92.5 | 86.9 | 82.8 | 75.3 | 73.0 | 73.0 | 67.0 | | | | | | | |
| | 10 | 100.0 | 93.3 | 91.5 | 85.2 | 79.5 | 73.1 | 70.3 | 72.4 | 69.6 | | | | | | | |
| | 11 | 100.0 | 94.6 | 91.2 | 83.1 | 77.8 | 73.9 | 69.7 | 68.2 | 61.3 | | | | | | | |
| | 12 | 100.0 | 94.0 | 95.1 | 86.3 | 81.1 | 73.0 | 71.6 | 69.8 | 64.9 | | | | | | | |

| | | | | | | | | | | | | | | | | |
|---|---|---|---|---|---|---|---|---|---|---|---|---|---|---|---|---|
| 5.2 Animal Weights As A Percentage of 0 | | | | | | | | | | | | | | | | |
| Treatment | Mouse Number | Day 0 | Day 1 | Day 2 | Day 3 | Day 4 | Day 5 | Day 6 | Day 7 | Day 8 | Day 9 | Day 10 | Day 11 | Day 12 | Day 13 | Day 14 | Day 15 |
| | 13 | 100.0 | 95.8 | 95.1 | 88.6 | 83.0 | 76.1 | 73.1 | | | | | | | | | |
| | 14 | 100.0 | 94.2 | 93.1 | 85.0 | 78.1 | 73.7 | 73.0 | 73.4 | 70.8 | 69.0 | | | | | | |
| | 15 | 100.0 | 93.5 | 91.7 | 86.6 | 79.0 | 74.3 | 69.9 | 66.7 | | | | | | | | |
| | 16 | 100.0 | 93.2 | 94.7 | 86.8 | 81.2 | 74.1 | 74.1 | 74.1 | 74.8 | 75.6 | | | | | | |
| | 17 | 100.0 | 96.9 | 96.2 | 88.1 | 81.9 | 75.8 | 73.8 | 72.3 | | | | | | | | |
| | 18 | 100.0 | 94.1 | 93.3 | 87.1 | 81.6 | 74.9 | | | | | | | | | | |
| | 19 | 100.0 | 91.9 | 91.9 | 85.7 | 80.9 | 74.6 | 72.4 | 67.3 | | | | | | | | |
| | 20 | 100.0 | 94.4 | 94.4 | 88.1 | 80.7 | 75.8 | 73.7 | 71.6 | 69.1 | 69.5 | | | | | | |
| | Mean | 100.0 | 94.7 | 93.8 | 87.2 | 82.1 | 75.6 | 73.3 | 72.4 | 72.5 | 76.8 | 76.9 | 77.8 | 77.4 | 86.9 | 85.4 | 83.5 |
| | SD | 0.0 | 1.5 | 1.6 | 1.8 | 2.4 | 2.1 | 2.5 | 4.1 | 7.9 | 7.3 | 9.4 | 11.2 | 15.5 | | | |
| 13.5Gy PBI BM5 EntericSorb | 21 | 100.0 | 96.8 | 95.4 | 89.4 | 85.5 | 81.6 | 80.5 | 75.9 | 69.5 | | | | | | | |
| | 22 | 100.0 | 94.7 | 95.5 | 83.0 | 78.1 | 73.2 | 74.7 | 75.8 | 76.6 | 73.2 | 69.1 | | | | | |
| | 23 | 100.0 | 93.0 | 93.8 | 85.2 | 80.9 | 73.9 | 72.0 | 68.5 | | | | | | | | |
| | 24 | 100.0 | 98.6 | 98.2 | 92.6 | 87.9 | 84.4 | 82.6 | 83.7 | 82.3 | 76.2 | | | | | | |
| | 25 | 100.0 | 94.9 | 94.2 | 86.6 | 80.8 | 73.2 | 70.3 | | | | | | | | | |
| | 26 | 100.0 | 92.5 | 91.8 | 87.7 | 85.1 | 78.4 | 77.2 | 73.9 | 70.9 | 67.2 | | | | | | |
| | 27 | 100.0 | 93.5 | 93.9 | 91.3 | 86.3 | 80.5 | 76.5 | 74.4 | 70.4 | | | | | | | |
| | 28 | 100.0 | 96.3 | 94.8 | 89.9 | 86.9 | 81.0 | 76.5 | 79.1 | 78.7 | 78.8 | 70.9 | | | | | |
| | 29 | 100.0 | 95.3 | 93.9 | 89.6 | 86.0 | 77.8 | 75.6 | 73.8 | 68.1 | | | | | | | |
| | 30 | 100.0 | 90.9 | 92.4 | 85.9 | 84.1 | 78.6 | 75.4 | 76.8 | 73.6 | 71.4 | | | | | | |
| | 31 | 100.0 | 94.9 | 96.7 | 89.5 | 84.0 | 78.9 | 75.3 | 71.6 | 70.2 | | | | | | | |
| | 32 | 100.0 | 97.9 | 99.6 | 91.4 | 86.4 | 81.1 | 78.9 | 79.3 | 70.7 | 66.1 | | | | | | |
| | 33 | 100.0 | 96.3 | 96.6 | 88.4 | 84.0 | 79.1 | 78.0 | 82.1 | 84.3 | 84.7 | 78.4 | 68.7 | | | | |
| | 34 | 100.0 | 93.5 | 95.0 | 90.6 | 84.5 | 76.3 | 72.7 | 76.3 | 69.8 | | | | | | | |
| | 35 | 100.0 | 91.6 | 95.4 | 88.2 | 83.3 | 76.4 | 76.0 | 80.2 | 82.9 | 86.3 | 77.2 | 76.0 | | | | |
| | 36 | 100.0 | 93.9 | 94.6 | 88.8 | 81.9 | 77.6 | 74.4 | 77.6 | 73.3 | | | | | | | |
| | 37 | 100.0 | 96.1 | 93.2 | 88.3 | 82.2 | 77.2 | 77.6 | 84.3 | 86.8 | 88.3 | 85.4 | 87.5 | 81.5 | 77.2 | 83.6 | 84.3 |
| | 38 | 100.0 | 96.1 | 97.6 | 88.2 | 81.5 | 74.8 | 73.6 | 70.9 | | | | | | | | |
| | 39 | 100.0 | 97.8 | 97.1 | 92.1 | 86.7 | 81.0 | 76.7 | 81.7 | 84.2 | 87.5 | 85.7 | 86.7 | 85.7 | 86.0 | 85.7 | 85.3 |
| | 40 | 100.0 | 95.8 | 98.5 | 91.6 | 85.2 | 78.3 | 77.9 | 79.5 | 79.1 | 83.3 | 80.6 | 74.9 | 69.6 | | | |
| | Mean | 100.0 | 95.0 | 95.4 | 88.9 | 84.1 | 78.2 | 76.1 | 77.1 | 76.0 | 78.4 | 78.2 | 78.8 | 78.9 | 81.6 | 84.6 | 84.8 |
| | SD | 0.00 | 2.1 | 2.1 | 2.5 | 2.5 | 3.0 | 2.9 | 4.4 | 6.3 | 8.2 | 6.5 | 8.1 | 8.3 | 6.2 | 1.4 | 0.7 |

| | | 5.3 Diarrhea Scores | | | | | | | | | | | | | | | | | | | | |
|---|---|---|---|---|---|---|---|---|---|---|---|---|---|---|---|---|---|---|---|---|---|---|
| Treatment | Mouse Number | Day 4 | | Day 5 | | Day 6 | | Day 7 | | Day 8 | | Day 9 | | Day 10 | | Day 11 | | Day 12 | | Day 13 | | Day 14 | |
| | | AM | PM | AM | PM | AM | PM | AM | PM | AM | PM | AM | PM | AM | PM | AM | PM | AM | PM | AM | PM | AM | PM |
| 13.5Gy PBI BM5 Vehicle | 1 | 0 | 0 | 0 | 0 | 1 | 0 | 0 | 0 | | | | | | | | | | | | | | | |
| | 2 | 0 | 0 | 0 | 0 | 1 | 0 | 0 | 0 | | | | | | | | | | | | | | | |
| | 3 | 0 | 0 | 0 | 0 | 0 | 0 | 0 | 0 | 0 | 0 | 0 | 0 | 0 | 0 | 0 | 0 | 0 | | | | | |
| | 4 | 0 | 0 | 1 | 0 | 1 | 0 | 0 | | | | | | | | | | | | | | | | |
| | 5 | 0 | 0 | 0 | 0 | 0 | 0 | 0 | 0 | 0 | 0 | 0 | 0 | 0 | 0 | | | | | | | | | |
| | 6 | 0 | 1 | 1 | 0 | 1 | 0 | 0 | 0 | 0 | 0 | | | | | | | | | | | | | |
| | 7 | 0 | 0 | 1 | 0 | 1 | 0 | 0 | | | | | | | | | | | | | | | | |
| | 8 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| | 9 | 0 | 0 | 1 | 0 | 0 | 0 | 0 | 0 | 0 | | | | | | | | | | | | | | |
| | 10 | 0 | 0 | 0 | 0 | 0 | 0 | 0 | 0 | | | | | | | | | | | | | | | |
| | 11 | 0 | 0 | 0 | 0 | 0 | 0 | 0 | 0 | | | | | | | | | | | | | | | |
| | 12 | 0 | 1 | 2 | 2 | 1 | 0 | 1 | 0 | 0 | | | | | | | | | | | | | | |
| | 13 | 0 | 1 | 1 | 0 | 1 | 0 | | | | | | | | | | | | | | | | | |
| | 14 | 0 | 0 | 1 | 1 | 1 | 0 | 0 | 0 | 0 | 0 | | | | | | | | | | | | | |
| | 15 | 2 | 2 | 2 | 2 | 2 | 2 | 1 | | | | | | | | | | | | | | | | |
| | 16 | 0 | 0 | 0 | 0 | 1 | 0 | 0 | 0 | 0 | 0 | | | | | | | | | | | | | |
| | 17 | 0 | 0 | 0 | 0 | 0 | 0 | 0 | | | | | | | | | | | | | | | | |
| | 18 | 0 | 0 | 0 | 1 | | | | | | | | | | | | | | | | | | | |
| | 19 | 0 | 1 | 0 | 0 | 1 | 0 | 0 | 0 | | | | | | | | | | | | | | | |
| | 20 | 0 | 1 | 1 | 0 | 1 | 0 | 0 | 0 | 0 | 0 | 0 | | | | | | | | | | | | |
| | SUM | 2 | 7 | 11 | 6 | 13 | 2 | 2 | 0 | 0 | 0 | 0 | 0 | 0 | 0 | 0 | 0 | 0 | 0 | 0 | 0 | 0 | 0 |
| 13.5Gy PBI BM5 EntericSorb | 21 | 0 | 0 | 0 | 0 | 0 | 0 | 0 | 0 | | | | | | | | | | | | | | | |
| | 22 | 0 | 0 | 0 | 0 | 0 | 0 | 0 | 0 | 0 | 0 | 0 | 0 | | | | | | | | | | | |
| | 23 | 0 | 1 | 0 | 0 | 0 | 0 | 0 | | | | | | | | | | | | | | | | |
| | 24 | 0 | 0 | 0 | 0 | 0 | 0 | 0 | 0 | 0 | 0 | | | | | | | | | | | | | |
| | 25 | 0 | 0 | 1 | 0 | 1 | | | | | | | | | | | | | | | | | | |
| | 26 | 0 | 0 | 0 | 0 | 0 | 0 | 0 | 0 | 0 | 0 | | | | | | | | | | | | | |
| | 27 | 0 | 0 | 0 | 0 | 0 | 0 | 0 | 0 | 0 | | | | | | | | | | | | | | |

5.3 Diarrhea Scores

| Treatment | Mouse Number | Day 4 AM | Day 4 PM | Day 5 AM | Day 5 PM | Day 6 AM | Day 6 PM | Day 7 AM | Day 7 PM | Day 8 AM | Day 8 PM | Day 9 AM | Day 9 PM | Day 10 AM | Day 10 PM | Day 11 AM | Day 11 PM | Day 12 AM | Day 12 PM | Day 13 AM | Day 13 PM | Day 14 AM | Day 14 PM |
|---|---|---|---|---|---|---|---|---|---|---|---|---|---|---|---|---|---|---|---|---|---|---|---|
| | 28 | 0 | 0 | 0 | 0 | 0 | 0 | 0 | 0 | 0 | 0 | 0 | 0 | 0 | | | | | | | | | |
| | 29 | 0 | 0 | 1 | 0 | 0 | 0 | 0 | 0 | 0 | | | | | | | | | | | | | |
| | 30 | 0 | 0 | 0 | 0 | 0 | 0 | 0 | 0 | 0 | 0 | 0 | 0 | | | | | | | | | | |
| | 31 | 0 | 0 | 0 | 0 | 0 | 0 | 0 | 0 | 0 | 0 | | | | | | | | | | | | |
| | 32 | 0 | 0 | 0 | 0 | 0 | 0 | 0 | 0 | 0 | 0 | 0 | | | | | | | | | | | |
| | 33 | 0 | 0 | 0 | 0 | 0 | 0 | 0 | 0 | 0 | 0 | 0 | 0 | 0 | 0 | 0 | | | | | | | |
| | 34 | 0 | 2 | 2 | 0 | 1 | 0 | 0 | 0 | 0 | | | | | | | | | | | | | |
| | 35 | 0 | 0 | 0 | 0 | 0 | 0 | 0 | 0 | 0 | 0 | 0 | 0 | 0 | 0 | 0 | 0 | | | | | | |
| | 36 | 0 | 0 | 1 | 0 | 0 | 0 | 0 | 0 | 0 | 0 | | | | | | | | | | | | |
| | 37 | 0 | 0 | 0 | 0 | 1 | 0 | 0 | 0 | 0 | 0 | 0 | 0 | 0 | 0 | 0 | 0 | 0 | 0 | 0 | 0 | 0 | 0 |
| | 38 | 0 | 0 | 1 | 0 | 0 | 0 | 0 | | | | | | | | | | | | | | | |
| | 39 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| | 40 | 0 | 0 | 1 | 0 | 1 | 0 | 0 | 0 | 0 | 0 | 0 | 0 | 0 | 0 | 0 | 0 | 0 | | | | | |
| SUM | | | 3 | 7 | 0 | 4 | 0 | 0 | 0 | 0 | 0 | 0 | 0 | 0 | 0 | 0 | 0 | 0 | 0 | 0 | 0 | 0 | 0 |

What is claimed:

1. A method comprising gastrointestinal administration of one or more enteron sorbent polymers to a subject that was exposed to radiation; wherein said enteron sorbent polymer is characterized as having a pore structure having a total volume of pore sizes in the range of from 10 Å to 250,000 Å greater than 0.3 cc/g to 3.0 cc/g dry polymer; wherein the ratio of pore volume between 10 Å to 250,000 Å in diameter to pore volume between 250 Å to 250,000 Å in diameter of the cross-linked polymeric material is smaller than 7:1 and wherein the ratio of pore volume between 10 Å to 250,000 Å in diameter to pore volume between 50 Å to 250,000 Å in diameter of the cross-linked polymeric material is less than 2:1.

2. The method of claim 1 where the radiation source of is cancer therapy.

3. The method of claim 1 where the source of radiation is gamma radiation, X-rays, or cosmic radiation, transmitted via radiation or through contamination of the air, food, or water.

4. The method of claim 1 wherein said enteron sorbent polymer comprises cross-linked polymeric material derived from the reaction of a cross-linker with one or more of the following polymerizable monomers: styrene, ethylstyrene, acrylonitrile, butyl methacrylate, octyl methacrylate, butyl acrylate, octyl acrylate, cetyl methacrylate, cetyl acrylate, ethyl methacrylate, ethyl acrylate, vinyltoluene, vinylnaphthalene, vinylbenzyl alcohol, vinylformamide, methyl methacrylate, and methyl acrylate.

5. The method of claim 1 where the enteron sorbent polymers are administered via capsule, tablet, salve, poultice, in slurry form, suppository, or enema, via oral, rectal, nasogastric or gastric tube, or ostomy routes.

6. The method of claim 1 where the enteron sorbent polymers remove inflammatory mediators, comprising cytokines, superantigens, monokines, chemokines, interferons, free radicals, proteases, arachidonic acid metabolites, prostacyclins, beta endorphins, anandimide, 2-arachadonyl-glycerol, tetrahydrobiopterin, serotonin, histamine, bradykinin, soluble CD40 ligand, bioactive lipids, oxidized lipids, cell-free hemoglobin, growth factors, glycoproteins, prions, toxins, bacterial and viral toxins, endotoxins, drugs, vasoactive substances, foreign antigens, and antibodies from the gut lumen.

7. The method of claim 1 where the enteron sorbent polymers are biocompatible.

8. The method of claim 1 where the enteron sorbent polymers are in the form of a powder, suspension, beads or other regularly or irregularly shaped particulates.

9. The method of claim 1 where the enteron sorbent polymers have a diameter in the range of 0.1 microns to 2 centimeters.

10. The method of claim 1 where the enteron sorbent polymers are gamma radiation stable.

11. The method of claim 1 where the enteron sorbent polymers are gamma radiation stable and can be administered prior or concurrently to radiotherapy.

12. The method of claim 1 where the enteron sorbent polymers do not absorb or minimally absorb radiation (radiolucent) and therefore do not affect the radiotherapy dose to treat diseases.

13. The method of claim 1 where the enteron sorbent polymers absorb radiation (radiopaque) and provide additional radioprotection.

14. The method of claim 1 where the enteron sorbent polymers function as radioprotectants that enable higher and potentially more effective doses of radiotherapy, or more doses of radiotherapy, to treat cancer while mitigating acute radiation enteritis or colitis.

15. A method comprising gastrointestinal administration of one or more enteron sorbent polymers to a subject prior to exposure to radiation, wherein said enteron sorbent polymer is characterized as having a pore structure having a total volume of pore sizes in the range of from 10 Å to 250,000 Å greater than 0.3 cc/g to 3.0 cc/g dry polymer; wherein the ratio of pore volume between 10 Å to 250,000 Å in diameter to pore volume between 250 Å to 250,000 Å in diameter of the cross-linked polymeric material is smaller than 7:1 and wherein the ratio of pore volume between 10 Å to 250,000 Å in diameter to pore volume between 50 Å to 250,000 Å in diameter of the cross-linked polymeric material is less than 2:1.

16. The method of claim 15, where the radiation is a component of cancer therapy.

17. The method of claim 15, wherein said enteron sorbent polymer comprises cross-linked polymeric material derived from the reaction of a cross-linker with one or more of the following polymerizable monomers: styrene, ethylstyrene, acrylonitrile, butyl methacrylate, octyl methacrylate, butyl acrylate, octyl acrylate, cetyl methacrylate, cetyl acrylate, ethyl methacrylate, ethyl acrylate, vinyltoluene, vinylnaphthalene, vinylbenzyl alcohol, vinylformamide, methyl methacrylate, and methyl acrylate.

18. The method of claim 15, where the enteron sorbent polymers are administered via capsule, tablet, salve, poultice, in slurry form, suppository, or enema, via oral, rectal, nasogastric or gastric tube, or ostomy routes.

19. The method of claim 15, where the enteron sorbent polymers are biocompatible.

20. The method of claim 15, where the enteron sorbent polymers are in the form of a powder, suspension, beads or other regularly or irregularly shaped particulates.

21. The method of claim 15, where the enteron sorbent polymers have a diameter in the range of 0.1 microns to 2 centimeters.

22. The method of claim 15, where the enteron sorbent polymers are gamma radiation stable.

* * * * *